US012637423B2

(12) United States Patent
Scheerder et al.

(10) Patent No.: US 12,637,423 B2
(45) Date of Patent: May 26, 2026

(54) AZIRIDINYL FUNCTIONAL COMPOUND

(71) Applicant: COVESTRO (NETHERLANDS) B.V., Geleen (NL)

(72) Inventors: Jurgen Scheerder, Geleen (NL); Gerardus Cornelis Overbeek, Geleen (NL); Patrick Johannes Maria Stals, Geleen (NL); Daan Van Der Zwaag, Geleen (NL); Alfred Jean Paul Bückmann, Geleen (NL); Hans Groen, Geleen (NL); Emilio Martin, Geleen (NL); Johannes Jacobus Julius Van Den Biggelaar, Geleen (NL)

(73) Assignee: Covestro (Netherlands) B.V., Geleen (NL)

(*) Notice: Subject to any disclaimer, the term of this patent is extended or adjusted under 35 U.S.C. 154(b) by 890 days.

(21) Appl. No.: 17/792,005

(22) PCT Filed: Jan. 21, 2021

(86) PCT No.: PCT/EP2021/051387

§ 371 (c)(1),
(2) Date: Jul. 11, 2022

(87) PCT Pub. No.: WO2021/148565

PCT Pub. Date: Jul. 29, 2021

(65) Prior Publication Data

US 2023/0312525 A1 Oct. 5, 2023

(30) Foreign Application Priority Data

| | | |
|---|---|---|
| Jan. 22, 2020 | (EP) | 20153154 |
| Jan. 22, 2020 | (EP) | 20153159 |
| Jan. 22, 2020 | (EP) | 20153239 |
| Jan. 22, 2020 | (EP) | 20153240 |
| Jan. 22, 2020 | (EP) | 20153242 |
| Jan. 22, 2020 | (EP) | 20153245 |
| Jan. 22, 2020 | (EP) | 20153246 |
| Jan. 22, 2020 | (EP) | 20153249 |
| Jan. 22, 2020 | (EP) | 20153250 |
| Jan. 22, 2020 | (EP) | 20153251 |
| Jan. 22, 2020 | (EP) | 20153253 |

(Continued)

(51) Int. Cl.
*C07D 403/12* (2006.01)
*C07D 203/10* (2006.01)
(Continued)

(52) U.S. Cl.
CPC ......... *C07D 203/10* (2013.01); *C07D 251/32* (2013.01); *C07D 403/12* (2013.01);
(Continued)

(58) Field of Classification Search
None
See application file for complete search history.

(56) References Cited

U.S. PATENT DOCUMENTS 3,329,674 A 7/1967 Bulbenko et al.
3,337,533 A 8/1967 Ham
(Continued)

FOREIGN PATENT DOCUMENTS

CN 1368524 A 9/2002
CN 1606574 A 4/2005
(Continued)

OTHER PUBLICATIONS

Grant & Hackh's Chemical Dictionary (5th Ed. 1987) at p. 148.*
International Search Report for PCT/EP2021/051387 dated May 18, 2021, 4 pages.
Written Opinion of the ISA for PCT/EP2021/051387 dated May 18, 2021, 6 pages.
Dahlquist et al.,"Contact allergy to trimethylolpropane triacrylate (TMPTA) in an aziridine plastic hardener", Contact Dermatitis, 1983, pp. 122-124, vol. 9.
Jiao.,"Preparation of Waterborne Polyurethane Based on Renewable Resources and Its Film Properties", Dissertation, Jun. 18, 2010, pp. 1-79, Dalian University of Technology.
Lee, SH. et al.,"Preparation and characterization of acrylic pressure—sensitive adhesives based on UV and heat curing systems", International Journal of Adhesion and Adhesives, Jun. 1, 2017, pp. 1-19, Issue 75.
(Continued)

*Primary Examiner* — Po-Chih Chen
(74) *Attorney, Agent, or Firm* — The Webb Law Firm

(57) ABSTRACT

The present invention relates to compound (I) comprising at least one functional group A and at least one functional group B, wherein the functional groups A has structural formula A: wherein $R_1$ is H, $R_2$, $R_3$ and $R_4$ are independently chosen from H, methyl or ethyl, m is 1-6; and the functional groups B has structural formula B: $R_5$ is H or methyl, X is O or NH, Z' is a polyalkoxy group or an omega-alkoxy polycaprolacton group, Y' is a collection of atoms covalently connected in linear or branched configuration n" is 0 or 1, and m' is an integer from 1-6; with the proviso that the summed amount of the number of functional groups A and the number of functional groups B in compound (I) is from 2-13; and the compound has a molecular weight in the range from 800-10000 Dalton.

(A)

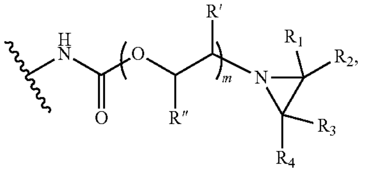

(B)

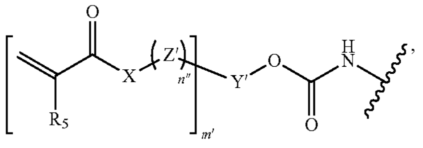

14 Claims, No Drawings

(30) Foreign Application Priority Data

| | | | |
|---|---|---|---|
| Jan. 24, 2020 | (EP) | .................................... | 20153628 |
| Jan. 24, 2020 | (EP) | .................................... | 20153630 |
| Jul. 24, 2020 | (EP) | .................................... | 20187717 |

(51) Int. Cl.

| | |
|---|---|
| ***C07D 251/32*** | (2006.01) |
| ***C07D 403/14*** | (2006.01) |
| ***C07D 413/14*** | (2006.01) |
| ***C07D 487/14*** | (2006.01) |
| ***C08F 220/18*** | (2006.01) |
| ***C08G 18/02*** | (2006.01) |
| ***C08G 18/08*** | (2006.01) |
| ***C08G 18/12*** | (2006.01) |
| ***C08G 18/22*** | (2006.01) |
| ***C08G 18/24*** | (2006.01) |
| ***C08G 18/28*** | (2006.01) |
| ***C08G 18/30*** | (2006.01) |
| ***C08G 18/32*** | (2006.01) |
| ***C08G 18/34*** | (2006.01) |
| ***C08G 18/38*** | (2006.01) |
| ***C08G 18/42*** | (2006.01) |
| ***C08G 18/44*** | (2006.01) |
| ***C08G 18/48*** | (2006.01) |
| ***C08G 18/66*** | (2006.01) |
| ***C08G 18/67*** | (2006.01) |
| ***C08G 18/73*** | (2006.01) |
| ***C08G 18/75*** | (2006.01) |
| ***C08G 18/76*** | (2006.01) |
| ***C08G 18/79*** | (2006.01) |
| ***C08G 18/83*** | (2006.01) |
| ***C08K 5/3412*** | (2006.01) |
| ***C08K 5/3492*** | (2006.01) |
| ***C08L 63/00*** | (2006.01) |
| ***C09D 7/20*** | (2018.01) |
| ***C09D 7/45*** | (2018.01) |
| ***C09D 7/63*** | (2018.01) |
| ***C09D 7/65*** | (2018.01) |
| ***C09D 11/101*** | (2014.01) |
| ***C09D 133/02*** | (2006.01) |
| ***C09D 133/04*** | (2006.01) |
| ***C09D 175/04*** | (2006.01) |
| ***C09D 175/08*** | (2006.01) |
| ***C09D 175/12*** | (2006.01) |

(52) U.S. Cl.

CPC ......... *C07D 403/14* (2013.01); *C07D 413/14* (2013.01); *C07D 487/14* (2013.01); *C08F 220/1804* (2020.02); *C08G 18/027* (2013.01); *C08G 18/0823* (2013.01); *C08G 18/0866* (2013.01); *C08G 18/12* (2013.01); *C08G 18/227* (2013.01); *C08G 18/246* (2013.01); *C08G 18/282* (2013.01); *C08G 18/2825* (2013.01); *C08G 18/283* (2013.01); *C08G 18/2865* (2013.01); *C08G 18/2875* (2013.01); *C08G 18/302* (2013.01); *C08G 18/3228* (2013.01); *C08G 18/3231* (2013.01); *C08G 18/3275* (2013.01); *C08G 18/348* (2013.01); *C08G 18/3842* (2013.01); *C08G 18/4291* (2013.01); *C08G 18/44* (2013.01); *C08G 18/4808* (2013.01); *C08G 18/4825* (2013.01); *C08G 18/4854* (2013.01); *C08G 18/4862* (2013.01); *C08G 18/4879* (2013.01); *C08G 18/6692* (2013.01); *C08G 18/6715* (2013.01); *C08G 18/73* (2013.01); *C08G 18/755* (2013.01); *C08G 18/758* (2013.01); *C08G 18/765* (2013.01); *C08G 18/792* (2013.01); *C08G 18/798* (2013.01); *C08G 18/833* (2013.01); *C08K 5/3412* (2013.01); *C08K 5/34924* (2013.01); *C08K 5/34926* (2013.01); *C08L 63/00* (2013.01); *C09D 7/20* (2018.01); *C09D 7/45* (2018.01); *C09D 7/63* (2018.01); *C09D 7/65* (2018.01); *C09D 11/101* (2013.01); *C09D 133/02* (2013.01); *C09D 133/04* (2013.01); *C09D 175/04* (2013.01); *C09D 175/08* (2013.01); *C09D 175/12* (2013.01); *C08G 2150/00* (2013.01)

(56) References Cited

U.S. PATENT DOCUMENTS

| | | | | |
|---|---|---|---|---|
| 3,523,750 | A | 8/1970 | Tesoro | |
| 3,560,415 | A | 2/1971 | Grögler et al. | |
| 3,583,977 | A | 6/1971 | Uelzmann | |
| 3,763,132 | A | 10/1973 | Meiser | |
| 3,933,936 | A | 1/1976 | Smith et al. | |
| 4,605,698 | A | 8/1986 | Briden | |
| 5,106,993 | A | 4/1992 | Kania | |
| 5,133,997 | A | 7/1992 | Maier et al. | |
| 5,164,467 | A | 11/1992 | Kania | |
| 5,241,001 | A | 8/1993 | Kania et al. | |
| 5,258,481 | A | 11/1993 | Hesselmans et al. | |
| 5,359,005 | A | 10/1994 | Kania et al. | |
| 7,294,449 | B1 | 11/2007 | Gudeman et al. | |
| 7,396,891 | B2 | 7/2008 | Gray et al. | |
| 8,318,855 | B2 | 11/2012 | Schafheutle et al. | |
| 12,180,194 | B2 * | 12/2024 | Overbeek | C09D 133/12 |
| 2007/0298006 | A1 | 12/2007 | Tomalia et al. | |
| 2008/0114096 | A1 | 5/2008 | Qu et al. | |
| 2015/0118501 | A1 | 4/2015 | Lu et al. | |
| 2017/0218110 | A1 | 8/2017 | Arzt et al. | |
| 2021/0332031 | A1 * | 10/2021 | Overbeek | C07D 403/14 |

FOREIGN PATENT DOCUMENTS

| | | | |
|---|---|---|---|
| CN | 101437863 | A | 5/2009 |
| CN | 102046688 | A | 5/2011 |
| CN | 108084870 | | 5/2018 |
| EP | 0 507 407 | | 10/1992 |
| EP | 0 758 662 | | 2/1997 |
| EP | 1865014 | | 12/2007 |
| GB | 1344725 | | 1/1974 |
| JP | 47-027971 | | 8/1972 |
| JP | 51-141860 | | 5/1976 |
| JP | 59-128291 | | 7/1984 |
| JP | 11-500152 | | 1/1999 |
| JP | 2012-529473 | | 11/2012 |
| JP | 2015-505889 | | 2/2015 |
| WO | 2006/115547 | | 11/2006 |
| WO | 2013/089927 | | 6/2013 |
| WO | 2015/066868 | | 5/2015 |
| WO | 2020/020714 | | 1/2020 |

OTHER PUBLICATIONS

Zhang et al., "Study on Heat Resistance of Polyurethane-imide Silicone Modified Epoxy Coatings," Aging and Application of Synthetic Materials, 2018, pp. 24-27, vol. 47, Issue 3.

* cited by examiner

AZIRIDINYL FUNCTIONAL COMPOUND

This application is the U.S. national phase of International Application No. PCT/EP2021/051387 filed Jan. 21, 2021 which designated the U.S. and claims priority to EP 20187717.2 filed Jul. 24, 2020, EP 20153628.1 filed Jan. 24, 2020, EP 20153630.7 filed Jan. 24, 2020, EP 20153154.8 filed Jan. 22, 2020, EP 20153159.7 filed Jan. 22, 2020, EP 20153239.7 filed Jan. 22, 2020, EP 20153240.5 filed Jan. 22, 2020, EP 20153242.1 filed Jan. 22, 2020, EP 20153245.4 filed Jan. 22, 2020, EP 20153246.2 filed Jan. 22, 2020, EP 20153249.6 filed Jan. 22, 2020, EP 20153250.4 filed Jan. 22, 2020, EP 20153251.2 filed Jan. 22, 2020, EP 20153253.8 filed Jan. 22, 2020.

The present invention relates to aziridinyl functional compounds and to the use of such compounds as adhesion promotor or reactive diluent in free radical curable compositions. The present invention further relates to the field of free radical curable compositions comprising at least one compound comprising at least two radical copolymerisable ethylenically unsaturated groups and at least one of such aziridinyl functional compound.

There is a global trend to protect food using printed packaging (instead of plain packaging with a printed adhesive label). A substantial part of this packaging concerns flexible plastic packaging. Preferably, packaging manufacturers wish to be able to print directly on to the packaging substrate. Therefore it is essential that an ink adheres well to the flexible substrate. The current state of the art uses solvent-based inks. The use of solvents in the application of a coating has the disadvantage that the solvent has to evaporate during the application process. The evaporating solvent must be captured and is not allowed to be emitted to the environment because the typical solvents that are used have negative environmental properties. The coating process therefore has to include a solvent capture system which adds to the cost of the process. Furthermore evaporation of solvent is not a very fast process and costs energy which limits the coating speed. The converter would like to print as fast as possible to shorten the production time. Thus, the solvent based systems have serious environmental pollution problems, and the disadvantage of long drying and cure times, or of high curing temperatures. Further in shrink sleeve applications, which uses heat sensitive substrates (to be able to shrink the sleeve around the bottles in a later stage of the process), the use of energy curable systems has the advantage that no heat is needed to evaporate the solvents and dry the ink. In view of this, there are several economical and technical advantages if a switch could be made to radiation-curable printing inks. Nevertheless, the market penetration of radiation-curable inks in flexo printing is still low. The main reason for this is that the present UV-curable printing inks do not show the combination of good adhesion, high cure response, non-genotoxicity and low migration properties i.e. the absence of components that have the potential to migrate into the packaged food. The current state-of-the-art fast-drying UV-curable systems for food packaging is that they show bad adhesion to flexible plastic substrates. The usual solution for bad adhesion is to add low molecular weight monomers as diluent/adhesion promotor however as no low functional monomers can be used for potential migration reasons, this is limiting the use of UV curable systems in printing and packaging applications. As a consequence UV curable formulations cannot be used in the most optimal way in many graphic arts applications and the penetration is quite low in printed flexible packaging. Therefore, the development of a UV-curable system which fulfils these requirements is highly desired and could facilitate further market penetration of radiation-curable systems into the printed flexible packaging industry. Also for the coatings industry adhesion to rigid plastic substrates is relevant. This typically concern rigid plastic substrates that are used for example for automotive applications, furniture, domestic appliances. Also for coating application on rigid plastics, the adhesion of UV-curable resins tends to be insufficient requiring the use of solvent-based primers to ensure sufficient adhesion. There is a clear need to eliminate these solvent-based primers from a SHE perspective.

Another solution to improve adhesion to a substrate is treating the substrate with an aziridinyl functional compound prior to applying a coating or ink to the substrate. Trimethylolpropane tris(2-methyl-1-aziridinepropionate), CAS number 64265-57-2, a polyfunctional aziridine crosslinker, is a well-known and very active adhesion promotor. This is for example described in U.S. Pat. No. 5,057,371. This compound however has an unfavourable genotoxic profile. There is a need in the industry to improve the safety, health and environmental profile of adhesives, inks and coatings and also of the substances used for preparing adhesives, inks and coatings. Genotoxicity describes the property of chemical or physical agents that cause any type of DNA damage, which may not always lead to a transmittable mutation. Mutagenicity refers to the induction of permanent transmissible DNA changes (as DNA composition or chromosome structure), which are retained in somatic cell division and passed onto progeny in germ cells. Genotoxicity must not be confused with mutagenicity. All mutagens are genotoxic whereas not all genotoxic substances are mutagenic.

The object of the present invention is to provide aziridinyl functional compounds which can be used as adhesion promotor or reactive diluent in free radical curable compositions and which compounds have reduced genotoxicity compared to at least trimethylolpropane tris(2-methyl-1-aziridinepropionate).

This object has surprisingly been achieved by providing a compound (I) comprising at least one functional group A and at least one functional group B, wherein the functional groups A has structural formula A:

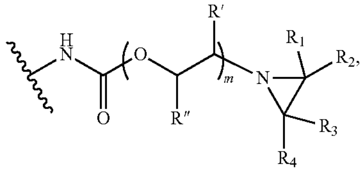

wherein $R_1$ is H, $R_2$, $R_3$ and $R_4$ are independently chosen from H, methyl or ethyl, R' and R'' are according to (1) or (2):

(1) R'=H or an aliphatic hydrocarbon group containing from 1 to 14 carbon atoms, and R''=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C═O)—R''', $CH_2$—O—R'''', or $CH_2$—(OCR''''''HCR''''''H)~-OR'''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R"""independently being H or an aliphatic hydrocarbon group containing from 1 to 14 carbon atoms and R""" being an aliphatic hydrocarbon group containing from 1 to 4 carbon atoms, (2) R' and R" form together a saturated cycloaliphatic hydrocarbon group containing from 5 to 8 carbon atoms; and the functional groups B has structural formula B:

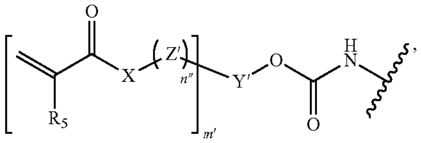

(B)

$R_5$ is H or methyl,

X is O or NH,

Z' is a polyalkoxy group or an omega-alkoxy polycaprolacton group,

Y' is a collection of atoms covalently connected in linear or branched configuration which collection of atoms consists of i) carbon and hydrogen atoms, ii) carbon, hydrogen and oxygen atoms, iii) carbon, hydrogen and nitrogen atoms, or iv) carbon, hydrogen, oxygen and nitrogen atoms, n" is 0 or 1, and m' is an integer from 1 to 6;

with the proviso that the summed amount of the number of functional groups A and the number of functional groups B in compound (I) is from 2 to 13; and the compound (I) has a molecular weight in the range from 600 Daltons to 10000 Dalton.

It has surprisingly been found that the compounds according to the invention have reduced genotoxicity compared to trimethylolpropane tris(2-methyl-1-aziridinepropionate). The compounds according to the invention show either only weakly positive induced genotoxicity or even they do not show genotoxicity, i.e. they show a genotoxicity level comparable with the naturally occurring background.

The genotoxicity can be measured by the ToxTracker® assay (Toxys, Leiden, the Netherlands) as further described herein. The ToxTracker® assay can be applied for pure substances or for compositions which are the direct products obtained in the preparation of the multi-aziridine compounds of the invention. With positive induced genotoxicity is meant that the induction level of the biomarkers Bscl2-GFP and Rtkn-GFP is equal to or higher than 2-fold at at least one of 10, 25 and 50% cytotoxicity in the absence or presence of the metabolizing system rat S9 liver extract. With weakly positive induced genotoxicity is meant that the induction level of the biomarkers Bscl2-GFP and Rtkn-GFP is higher than 1.5-fold and lower than 2-fold at at least one of 10, 25 and 50% cytotoxicity (but lower than 2-fold at 10, 25 and 50% cytotoxicity) in the absence or presence of rat S9 liver extract-based metabolizing systems (aroclor1254-induced rats, Moltox, Boone, NC, USA). With genotoxicity comparable with the naturally occurring background is meant that the induction level of the biomarkers Bscl2-GFP and Rtkn-GFP is less than or equal to 1.5-fold at 10, 25 and 50% cytotoxicity in the absence and presence of rat S9 liver extract-based metabolizing systems (aroclor1254-induced rats, Moltox, Boone, NC, USA). The induction level of the genotoxicity reporters Bscl2-GFP and Rtkn-GFP is preferably less than or equal to 1.5-fold at 10, 25 and 50% cytotoxicity in the absence and presence of rat S9 liver extract-based metabolizing systems (aroclor1254-induced rats, Moltox, Boone, NC, USA). A substance showing an induction level less than or equal to 1.5-fold at 10, 25 and 50% cytotoxicity in the absence and presence of rat S9 liver extract-based metabolizing systems (aroclor1254-induced rats, Moltox, Boone, NC, USA) is not genotoxic.

The compounds according to the invention improve the adhesion of a coating or ink to a substrate. Preferred substrates are plastic substrates, in particular low surface free energy plastic substrates, and substrates from wood plastic composite materials. Examples of low surface free energy plastic substrates are biaxially-oriented polypropylene (BOPP), polyethylene (PE) and polyethyleneteraphthalate (PET). Other substrates include PETG (Polyethylene Terephthalate Glycol), OPS (Oriented Polystyrene), PVC and PLA (Poly Lactic Acid Polylactide) (all used for shrink sleeve applications) and melamine coated substrates. Examples of rigid plastics include PVC, ABS, PP, PE, PS, EPDM, PC (polycarbonate), PA (polyamide), and combinations thereof. In addition, a very surprising and unexpected observation is that the improved adhesion is not only observed for (corona discharge) pretreated plastic substrates, but improved adhesion may also be observed for untreated plastic substrates. This allows to use untreated plastic substrates, but is also beneficial when using pretreated plastic substrates. The effect of corona or plasma treatment reduces in time due to surface reorganisations meaning that the surface tension in time decreases. This could mean that before applying a primer the previously treated plastic must be treated again to get sufficient adhesion. The fact that the compounds of the invention also adhere to untreated plastic removes the need for this additional treatment step. It makes the coating system must more robust as one does not need to check whether the previously treated plastic still has a surface free energy high enough for proper adhesion.

U.S. Pat. Nos. 3,523,750, 5,359,005, 5,164,467 and CN108084870 describe aziridine compounds which do not contain a functional group with structural formula B.

For all upper and/or lower boundaries of any range given herein, the boundary value is included in the range given, unless specifically indicated otherwise. Thus, when saying from x to y, means including x and y and also all intermediate values.

The term "aliphatic hydrocarbon group" refers to optionally branched alkyl, alkenyl and alkynyl group. The term "cycloaliphatic hydrocarbon group" refers to cycloalkyl and cycloalkenyl group optionally substituted with at least one aliphatic hydrocarbon group. The term "aromatic hydrocarbon group" refers to a benzene ring optionally substituted with at least one aliphatic hydrocarbon group. These optional aliphatic hydrocarbon group substituents are preferably alkyl groups. Examples of cycloaliphatic hydrocarbon groups with 7 carbon atoms are cycloheptyl and methyl substituted cyclohexyl. An example of an aromatic hydrocarbon group with 7 carbon atoms is methyl substituted phenyl. Examples of aromatic hydrocarbon groups with 8 carbon atoms are xylyl and ethyl substituted phenyl.

Functional Groups A

The compound (1) of the invention comprises at least one functional group A. The functional group A has structural formula A:

(A)

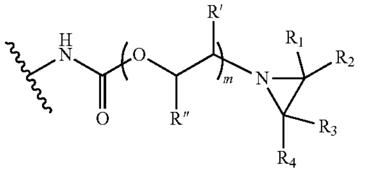

wherein $R_1$ is H, $R_2$, $R_3$ and $R_4$ are independently chosen from H, methyl or ethyl, R' and R'' are according to (1) or (2):

(1) R'=H or an aliphatic hydrocarbon group containing from 1 to 14 carbon atoms, and
   R''=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C═O)—R''', $CH_2$—O—R'''', or $CH_2$—(OCR'''''HCR'''''H)n-OR'''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R''''' independently being H or an aliphatic hydrocarbon group containing from 1 to 14 carbon atoms and R'''''' being an aliphatic hydrocarbon group containing from 1 to 4 carbon atoms, (2) R' and R'' form together a saturated cycloaliphatic hydrocarbon group containing from 5 to 8 carbon atoms.

In case the compound (I) according to the invention comprises more than one functional group A, the functional groups A present in the compound (I) according to the invention may independently have different $R_2$, $R_3$, $R_4$, R', R'' and/or m. The functional groups A present in the compound (1) are however preferably identical to each other.

The compound (I) according to the invention is usually obtained in a composition in which, next to the compound (1), remaining starting materials, side-products and/or solvent used for preparing the compound (1) may be present. The composition may contain only one compound (I) according to the invention but may also contain more than one compound (I) according to the invention. Mixtures of compounds (1) are for example obtained when a mixture of polyisocyanates as starting material are used.

The compound (I) according to the invention contains at least one functional group A, preferably from 1 to 3 of the functional groups A, more preferably 1 or 2 functional groups A, most preferably 1 functional group A.

In a preferred embodiment of the invention, $R_2$ is H, $R_3$ is $C_2H_5$ and $R_4$ is H. In another and more preferred embodiment of the invention, $R_2$ is H, $R_3$ is $CH_3$ and $R_4$ is $CH_3$. In another and even more preferred embodiment of the invention, $R_2$ is H, $R_3$ is $CH_3$ and $R_4$ is H.

m is an integer from 1 to 6, preferably m is from 1 to 4, more preferably m is 1 or 2 and most preferably m is 1.

Preferably, R' is H or an alkyl group containing from 1 to 2 carbon atoms. Most preferably R' is H.

R'' is preferably H, an aliphatic hydrocarbon group containing from 1 to 4 carbon atoms, $CH_2$—O—(C═O)—R''', $CH_2$—O—R'''', or $CH_2$—(OCR'''''HCR'''''H)$_n$—OR'''''', whereby R''' is an aliphatic hydrocarbon group containing from 1 to 12 carbon atoms and R'''' is an aliphatic hydrocarbon group containing from 1 to 12 carbon atoms or an aromatic hydrocarbon group containing from 6 to 12 carbon atoms, n being from 1 to 35, preferably from 6 to 20, R''''' independently being H or a methyl group and R'''''' being an alkyl group with 1 to 4 carbon atoms, or R' and R'' may be part of the same saturated cycloaliphatic hydrocarbon group containing from 5 to 8 carbon atoms. More preferably, R''=H or an alkyl group containing from 1 to 4 carbon atoms. Even more preferably, R''=an alkyl group containing from 1 to 4 carbon atoms. Even more preferably R'' is methyl.

Preferably, R' is H and R'' is methyl.

The functional groups A are preferably introduced into compound (1) according to the invention by using as raw material a compound A' with a structural formula as follows:

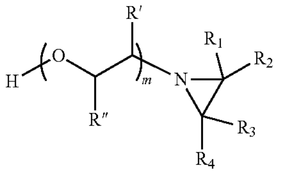

Methods for preparing compound A' and derivatives are known in the art. For example, synthesis of 1-(2-methyl-aziridin-1-yl)propan-2-ol is described by S. Lesniak, M. Rachwalski, S. Jarzynski, E. Obijalska Tetrahedron Asymm. 2013, 24 1336-1340. Synthesis of 1-(aziridin-1-yl)propan-2-ol is described by A. Baklien, M. V. Leeding, J. Kolm Aust. J. Chem. 1968, 21, 1557-1570. Preferred aziridine compounds used for preparing compounds A' are propylene imine and ethylaziridine. Synthesis of ethylaziridine is for example described in EP0227461B1. Most preferred aziridine compounds used for preparing compound A' is propylene imine The compound A' is preferably obtained by reacting at least a monoepoxide compound with an aziridine compound with the following structural formula (C):

(C)

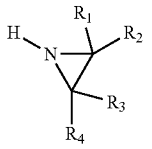

whereby $R_1$, $R_2$, $R_3$ and $R_4$ and its preferments are as defined above. The monoepoxide may be a mixture of different non-OH functional monoepoxides. Non-limited examples of monoepoxide are ethylene oxide, propylene oxide, 2-ethyl oxirane, n-butylglycidylether, 2-ethylhexylglycidylether, phenyl glycidyl ether, 4-tert-butylphenyl 2,3-epoxypropyl ether (=t-butyl phenyl glycidyl ether), cresol glycidyl ether (ortho or para) and glycidyl neodecanoate. The monoepoxide is preferably selected from the group consisting of propylene oxide, n-butylglycidylether (CAS number 2426-08-6), 2-ethylhexylglycidylether (CAS number 2461-15-6), glycidyl neodecanoate (CAS number 26761-45-5) and any mixture thereof.

The compound A' may also be obtained by reacting at least a diepoxide compound with an aziridine compound with structural formula (C) as given above. The diepoxide is preferably selected from the group consisting of bisphenol A diglycidyl ether (CAS No. 1675-54-3), neopentyl glycol diglycidyl ether (CAS No. 17557-23-2), butanediol diglycidyl ether (CAS No. 2425-79-8), ethylene glycol diglycidyl ether (CAS No. 2224-15-9), 1,6-Hexanediol diglycidyl ether (CAS No. 16096-31-4), polypropyleneglycol diglycidyl ether (CAS No. 26142-30-3), Poly(ethylene glycol) diglycidyl ether (CAS No. 72207-80-8) and any mixture thereof.

The compound A' is for example obtained in a process comprising at least the following step (i) by carrying out, for example, by bringing one equivalent of the epoxide compound into contact with one equivalent of the aziridine compound at a temperature in the range of from 20° C. to 110° C., more suitable from 40° C. to 95° C., even more suitable from 60 to 85° C. at atmospheric pressure. The aziridine compound is preferably propylene imine (CAS number 75-55-8) or 2,2-dimethylaziridine (CAS number 2658-24-4), more preferably the aziridine is propylene imine.

Functional Group B

The compound (I) of the invention comprises at least 1 functional group B, preferably at least 2 functional groups B, more preferably 2 functional groups B.

The functional group B has structural formula B:

(B)

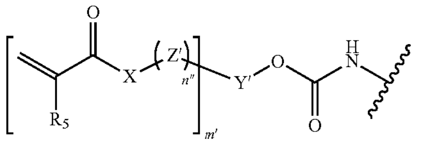

wherein $R_5$ is H or methyl,

X is O or NH,

Z' is a polyalkoxy group or an omega-alkoxy polycaprolacton group,

Y' is a collection of atoms covalently connected in linear or branched configuration which collection of atoms consists of i) carbon and hydrogen atoms, ii) carbon, hydrogen and oxygen atoms, iii) carbon, hydrogen and nitrogen atoms, or iv) carbon, hydrogen, oxygen and nitrogen atoms, n" is 0 or 1, and m' is an integer from 1 to 6.

In case the compound (I) according to the invention comprises more than one functional group (B), the functional groups (B) present in the compound (1) according to the invention may independently have different $R_5$, X, Z', Y', n" and/or m'. The functional groups (B) present in the compound (1) are however preferably identical to each other.

$R_5$ is preferably H resulting in that compound (I) has acryloyl groups as free radical curable groups.

X is preferably O resulting in that compound (I) has (meth)acryloyl ester groups as free radical curable groups.

Preferably $R_5$ is H and X is O resulting in that compound (1) has acryloyl ester groups as free radical curable groups.

Z' is a polyalkoxy group or an omega-alkoxy polycaprolacton group. The polyalkoxy group preferably has from 1 to 10 alkoxy repeating units, more preferably from 3 to 6 alkoxy repeating units, which alkoxy repeating units are preferably ethoxy, propoxy or butoxy repeating units. The omega-alkoxy polycaprolacton group preferably has from 2 to 6 repeating units, more preferably from 3 to 6 repeating units.

n" is 0 or 1.

m' is an integer from 1 to 6. In one embodiment, m' is 1. In this embodiment, the number of functional groups B is preferably 1 or 2 and the number of functional groups A is preferably 1 or 2; more preferably, the number of functional groups B is 2 and the number of functional groups A is 1. In another and more preferred embodiment, m' is from 2 to 6. In this embodiment, the number of functional groups B is preferably 1 and the number of functional groups A is preferably 1 or 2, more preferably the number of functional groups A is 1.

Preferably, Y' is a collection of atoms covalently connected in linear or branched configuration which collection of atoms consists of i) carbon and hydrogen atoms, ii) carbon, hydrogen and oxygen atoms, or iii) carbon, hydrogen, oxygen and nitrogen atoms. Preferably Y' consists of at most 100 atoms.

The functional group B is preferably introduced into compound (I) according to the invention by using as raw material a compound B' with a structural formula as follows:

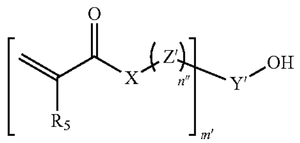

Non-limited examples of compounds B' which can be used in the present invention to chemically incorporate functional group B in compound (I) are hydroxyethyl(meth)acrylate, hydroxypropyl(meth)acrylate, hydroxybutyl(meth)acrylate, trimethylolpropane di(meth)acrylate and their (poly)ethoxylated and/or (poly)propoxylated equivalents, pentaerythritol tri(meth)acrylate and their (poly)ethoxylated and/or (poly)propoxylated equivalents, di(trimethylolpropane) tri(meth)acrylate and their (poly)ethoxylated and/or (poly)propoxylated equivalents, dipentaerythritol penta(meth)acrylate and their (poly)ethoxylated and/or (poly)propoxylated equivalents, glycerol diacrylate and their (poly)ethoxylated and/or (poly)propoxylated equivalents, polycaprolactone (meth)acrylate, polypropylene glycol acrylate, the amino ethanol Michael adducts of optionally alkoxylated trimethylolpropane tri(meth)acrylate, the amino ethanol Michael adducts of glycerol propoxylated tri (meth) acrylate end the amino ethanol Michael adducts of pentaerythritol tetra(meth)acrylate and any mixture thereof. Preferred compounds B' are hydroxyethyl(meth)acrylate, hydroxypropyl(meth)acrylate, hydroxybutyl(meth)acrylate and any mixture thereof and/or trimethylolpropane di(meth)acrylate, pentaerythritol tri(meth)acrylate and their (poly)ethoxylated and/or (poly)propoxylated equivalents, dipentaerythritol penta(meth)acrylate and their (poly)ethoxylated and/or (poly)propoxylated equivalents, di(trimethylolpropane) tri(meth)acrylate and their (poly)ethoxylated and (poly)propoxylated equivalents, polycaprolactone (meth)acrylate, polypropylene glycol acrylate, the amino ethanol Michael adducts of optionally alkoxylated trimethylolpropane tri(meth)acrylate, the amino ethanol Michael adducts of glycerol propoxylated tri (meth)acrylate end the amino ethanol Michael adducts of pentaerythritol tetra(meth)acrylate and any mixture thereof. Non limited examples of polypropylene glycol acrylate is Bisomer PPA6 (polypropyleneglycol monoacrylate), CAS number 50858-51-0, available from Geo specialty chemicals, such as Bisomer PPM5 Polypropyleneglycol (5) Methacrylate, Bisomer PEA6 Polyethyleneglycol (6) acrylate and Bisomer PEM6 Polyethyleneglycol (6) methacrylate. Non limited examples of polycaprolactone (meth)acrylates made by reacting hydroxyethylacrylate HEA or hydroxyethylmethacrylate HEMA with caprolactone are available from Daicel, such as Placcel FM series (based on HEMA) and Placcel FA series (based on HEA). Another suitable example of polycaprolactone acrylate is Sartomer 495B available from Arkema (reaction product of HEA and caprolactone (2-Oxepanone, homopolymer, 2-[(1-oxo-2-propen-1-yl)oxy]ethyl ester, Cas nr 110489-05-9)). In case $R_5$ is methyl, examples of compounds B' are the methacrylate variant of the above mentioned compounds. In case $R_5$ is H, examples of compounds B' are the acrylate variant of the above mentioned compounds.

In the embodiment wherein m' is 1, compound B' is preferably hydroxyethyl(meth)acrylate, hydroxypropyl (meth)acrylate, hydroxybutyl(meth)acrylate and any mixture thereof. In the embodiment wherein m' is from 2 to 6, compound B' is preferably trimethylolpropane di(meth)acrylate, pentaerythritol tri(meth)acrylate and their (poly) ethoxylated and/or (poly)propoxylated equivalents, dipentaerythritol penta(meth)acrylate and their (poly)ethoxylated and/or (poly)propoxylated equivalents, di(trimethylolpropane) tri(meth)acrylate and their (poly)ethoxylated and (poly)propoxylated equivalents, polycaprolactone (meth) acrylate, polypropylene glycol acrylate, the amino ethanol Michael adducts of optionally alkoxylated trimethylolpropane tri(meth)acrylate, the amino ethanol Michael adducts of glycerol propoxylated tri (meth)acrylate end the amino ethanol Michael adducts of pentaerythritol tetra(meth)acrylate and any mixture thereof.

The compound (I) of the invention preferably has structural formula $(A)_p$-W—$(B)_q$, wherein functional groups A and B are as defined above, p and q are independently an integer of at least 1, p+q is an integer from 2 to 13 and W preferably consists of a collection of atoms covalently connected in a linear or branched configuration which collection of atoms consists of: i) carbon and hydrogen atoms, ii) carbon, hydrogen and oxygen atoms, iii) carbon, hydrogen and nitrogen atoms, iv) carbon, hydrogen, oxygen and nitrogen atoms, or v) carbon, hydrogen and sulphur atoms. More preferably, W consists of a collection of atoms covalently connected in a linear or branched configuration which collection of atoms consists of: i) carbon and hydrogen atoms, ii) carbon, hydrogen and oxygen atoms, iii) carbon, hydrogen and nitrogen atoms, or iv) carbon, hydrogen, oxygen and nitrogen atoms. p is preferably 1 or 2. In one embodiment, m' in structural formula (B) is 1. In this embodiment, q is preferably 1 or 2 and p is preferably 1 or 2. More preferably, q is 1 and p is 2. In another and more preferred embodiment, m' in structural formula (B) is from 2 to 6. In this embodiment, q is preferably 1 and p is preferably 1 or 2, more preferably p is 1.

Even more preferably, W preferably consists of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof. Even more preferably, W consists of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, urethane functionality, urea functionality, biuret functionality and any combination thereof. W preferably contains an isocyanurate functionality, an iminooxadiazindione functionality, a biuret functionality, allophanate functionality or an uretdione functionality. More preferably, W contains an isocyanurate functionality or an iminooxadiazindione functionality. For the sake of clarity, the compound (I) of the invention may be obtained from the reaction product of one or more suitable compounds A' and B' and a hybrid isocyanurate such as for example a HDI/IPDI isocyanurate, resulting in a compound with a connecting group consisting of the array of the following consecutive functionalities: a linear $C_6H_{12}$ (i.e. an aliphatic hydrocarbon functionality with 6 carbon atoms), an isocyanurate functionality (a cyclic $C_3N_3O_3$) and

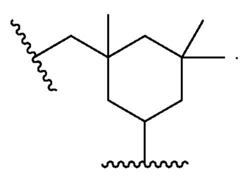 [SMILES: *CC1(C)CC(*)CC(C)(C)C1]

(i.e. a cycloaliphatic hydrocarbon functionality with 9 carbon atoms and an aliphatic hydrocarbon functionality with 1 carbon atom).

An aziridinyl group has the following structural formula:

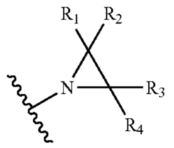

An isocyanurate functionality is defined as

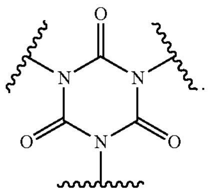 [SMILES: *n1c(=O)n(*)c(=O)n(*)c1=O]

An iminooxadiazindione functionality is defined as

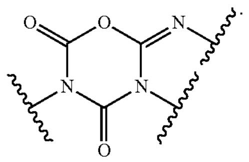 [SMILES: */N=c1/oc(=O)n(*)c(=O)n1*]

An allophanate functionality is defined as

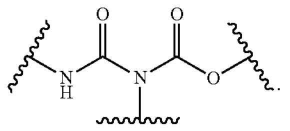 [SMILES: *NC(=O)N(*)C(=O)O*]

An uretdione functionality is defined as

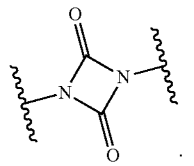 [SMILES: *N1C(=O)N(*)C1=O]

A biuret functionality is defined as

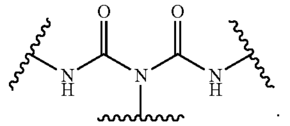 [SMILES: *NC(=O)N(*)C(=O)N*]

In a preferred embodiment of the invention, W consists of the following functionalities: at least one aliphatic hydrocarbon functionality and/or at least one cycloaliphatic hydrocarbon functionality and optionally at least one aromatic hydrocarbon functionality and optionally an isocyanurate functionality or iminooxadiazindione functionality or allophanate functionality or uretdione functionality. Preferably, W consists of the following functionalities: at least one aliphatic hydrocarbon functionality and/or at least one cycloaliphatic hydrocarbon functionality and optionally at least one aromatic hydrocarbon functionality and optionally an isocyanurate functionality or iminooxadiazindione functionality. More preferably, W consists of at least one aliphatic hydrocarbon functionality and/or at least one cycloaliphatic hydrocarbon functionality, and an isocyanurate functionality or an iminooxadiazindione functionality.

The group W is preferably introduced into compound (I) according to the invention by using as raw material compound W' being at least one polyisocyanate and/or at least one isocyanate terminated polyurethane (urea).

The polyisocyanate preferably has aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Compounds based on polyisocyanate with aliphatic reactivity have a reduced tendency of yellowing over time when compared to a similar compound but based on polyisocyanate with aromatic reactivity. The term "a polyisocyanate with aromatic reactivity" being intended to mean compounds in which all of the isocyanate groups are directly bonded to a benzene or naphthalene group, irrespective of whether aliphatic or cycloaliphatic groups are also present. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, p-tetra-methylxylene diisocyanate (p-TMXDI) and its meta isomer, and higher molecular weight variants like for example their isocyanurates or iminooxadiazindiones or allophanates or uretdiones. More preferred polyisocyanates with aliphatic reactivity are 4,4'-dicyclohexyl methane diisocyanate H12MDI, m-TMXDI, an isocyanurate or iminooxadiazindione or allophanate or uretdione of 1,6-hexamethylene diisocyanate and an isocyanurate of 1,5-pentamethylene diisocyanate. A suitable HDI containing iminooxadiazindione trimer is Desmodur® N3900, obtainable from Covestro. A suitable HDI containing allophonate is Desmodur® XP2860, obtainable from Covestro. A suitable HDI containing uretdione is Desmodur® N3400, obtainable from Covestro. Suitable HDI based isocyanurates trimers can for example be obtained from Covestro (Desmodur® N3600), Vencorex (Tolonate™ HDT LV), Asahi Kasei (Duranate™ TPA-100), Evonik (Vestanat® HT 2500/LV) and Tosoh (Coronate® HXR LV).

The isocyanate terminated polyurethane (urea) has a NCO/OH ratio higher than 1 and preferably lower than 1.6, more preferably lower than 1.4, even more preferably lower than 1.2 and most preferably lower than 1.15 and is obtained by reacting at least one polyol with at least one polyisocyanate. Preferred polyisocyanates are as described above. The polyol is preferably selected from the group consisting of polyether polyols, polythioether polyols, polyester polyols polycarbonate polyols, polyacetal polyols, polyvinyl polyols, polysiloxane polyols and any mixture thereof. More preferably the polyol is selected from the group consisting of polyether polyols and any mixture thereof. Preferred polyether polyols are polytetrahydrofuran, polyethylene oxide, polypropylene oxide or any mixture thereof.

The molecular weight of the compound (I) according to the invention is from 600 to 5000 Daltons. The molecular weight of the compound (1) according to the invention is preferably at most 3800 Daltons, more preferably at most 3600 Daltons, more preferably at most 3000 Daltons, more preferably at most 1600 Daltons. The molecular weight of the compound (I) according to the invention is preferably at least 700 Daltons, more preferably at least 750 Daltons, even more preferably at least 800 Daltons and most preferably at least 1000 Daltons. As used herein, the molecular weight of the compound (1) according to the invention is determined using MALDI-TOF mass spectrometry as described in the experimental part below.

The summed amount of the number of functional groups A and the number of functional groups B in compound (I) is from 2 to 13. The summed amount of the number of functional groups A and the number of functional groups B is preferably from 3 to 10, more preferably from 3 to 7, even more preferably is 3. In the embodiment where the summed amount of the number of functional groups A and the number of functional groups B is 3, p and q in structural formula $(A)_p$-W—$(B)_q$ and m' in structural unit B are preferably according to (i) p is 1 and q is 2 and m' is 1, or (ii) p is 1 and q is 1 and m' is 2, or (iii) p is 2 and q and m' are both 1.

In this embodiment, the compound (I) has 1 functional group A and 2 (meth)acryloyl functionalities or the compound has 2 functional groups A and 1 (meth)acryloyl functionality.

The compound (1) according to the invention is preferably obtained in a process comprising reacting compound A', compound B' and compound W' for at a temperature in the range of from 20° C. to 110° C., more suitable from 40° C. to 95° C., even more suitable from 60 to 85° C. at atmospheric pressure. The types and amounts of the compounds A', B' and W' are chosen such that the desired amount of functional groups A, the desired amount of functional groups B and the desired amount of (meth) acryloyl functionalities in functional group B is obtained.

The compound (1) according to the invention can also be obtained in a process comprising reacting compound A' with an isocyanate terminated polyurethane with (meth)acryloyl functional groups.

The present invention further relates to a crosslinker composition comprising at least one compound (I) as defined above and usually further comprising at least one additional component, such as for example remaining starting materials, side-products and/or solvent used in the preparation of the compound (I) according to the invention. The crosslinker composition may contain only one compound (I) according to the invention but may also contain more than one compound (I) according to the invention. Mixtures of compounds (I) are for example obtained when a mixture of polyisocyanates as starting material to prepare the compound (I) are used. After having obtained the compound(s) (I) according to the invention, the compound(s) (I) according to the invention may be separated, the reaction product may be used without further purification or solvent used for preparing the compound(s) (I) may be removed from the composition obtained in the preparation of the compound(s) (I) of the invention. The amount of compounds (I) according to the invention in the crosslinker composition is usually at least 10 wt. %, usually often at least 15 wt. % and most often at least 25 wt. % relative to total amount of the crosslinker composition. The amount of compounds (1) according to the invention in the crosslinker composition is preferably at least 60 wt. %, more preferably at least 80 wt. % and most preferably at least 99 wt. %, relative to total amount of the crosslinker composition. The molecular weight of the compounds (I) in the crosslinker composition is in the range of from 600 Daltons to 10000 Daltons. Preferred molecular weights are as described above and molecular weights of the compounds (I) are determined using MALDI-TOF-MS as described in the experimental part herein below. MALDI-TOF-MS means matrix-assisted laser desorption ionization time of flight mass spectroscopy.

The amount of aziridinyl group functional molecules, present in the crosslinker composition according to the invention, having a molecular weight lower than 250 Daltons, more preferably lower than 350 Daltons, even more preferably lower than 450 Daltons, even more preferably lower than 550 Daltons and even more preferably lower than 580 Daltons is preferably lower than 5 wt. %, more preferably lower than 2 wt. %, more preferably lower than 1 wt. %, more preferably lower than 0.5 wt. % and most preferably lower than 0.1 wt. %, relative to the total weight of the crosslinker composition, whereby the molecular weight is determined using LC-MS as described in the experimental part below.

The present invention further relates to compositions which are curable by free radical polymerization and which contain at least one aziridinyl functional compound as adhesion promotor having reduced genotoxicity compared to trimethylolpropane tris(2-methyl-1-aziridinepropionate). The aziridinyl functional compounds show either only weakly positive induced genotoxicity or even they do not show genotoxicity, i.e. they show a genotoxicity level comparable with the naturally occurring background. Furthermore it has surprisingly been found that the compositions according to the invention show improved adhesion while the amount of components that have the potential to migrate from the composition and especially from the cured composition (further referred to as migratables) is not increased and preferably even reduced.

Accordingly, the present invention further relates to a composition curable by free radical polymerization comprising

- at least one aziridinyl functional compound (I) having a molecular weight of from 600 to 10000 Daltons and having at least one functional group A and no or at least one functional group B, wherein functional group A and functional group B are as defined above,
- with the proviso that the summed amount of the number of functional groups A and the number of functional groups B in compound (1) is from 2 to 13, preferably from 3 to 10, more preferably from 3 to 7, even more preferably 3, and
- at least one compound (II) comprising at least two radical copolymerisable ethylenically unsaturated groups.

In one embodiment of the invention, the composition curable by free radical polymerization comprises an aziridinyl functional compound (1) having from 3 to 6 functional groups A and no functional group B. In this embodiment, said aziridinyl functional compound (I) preferably has 3 functional groups A. Said aziridinyl functional compound (I) having 3 functional groups A can be obtained by reacting at least compound A‘ and compound W’.

The composition curable by free radical polymerization preferably comprises at least one compound (11) comprising at least two radical copolymerisable ethylenically unsaturated groups, and

- at least one aziridinyl functional compound (I) having a molecular weight of from 600 to 10000 Daltons and having at least one functional group A and at least one functional group B, wherein functional group A and functional group B are as defined above, with the proviso that the summed amount of the number of functional groups A and the number of functional groups B in compound (I) is from 2 to 13. The summed amount of the number of functional groups A and the number of functional groups B in compound (I) is preferably from 3 to 10, more preferably the summed amount of the number of functional groups A and the number of functional groups B in compound (I) is from 3 to 7, even more preferably is 3.

The compounds (II) comprising at least two radical copolymerisable ethylenically unsaturated groups preferably have a number average of at least two unsaturated (C═C) groups which under the influence of irradiation (optionally in combination with the presence of a photo-initiator) can undergo crosslinking by free radical copolymerization.

The composition of the present invention is preferably radiation-curable. By radiation-curable is meant that radiation is required to initiate crosslinking of the composition. Optionally a photoinitiator (PI) may be added to the radiation-curable composition of the invention to assist radiation curing, especially if curing is by UV radiation. However, if curing is to be achieved by, for example, electron beam (EB) then a PI may not be needed. Preferably, the radiation-curable composition of the invention comprises a photoinitiator and UV-radiation is applied to obtain a cured coating. Thus the composition is preferably UV radiation curable. More preferably, the composition is 100% radiation-curable (substantially free of water and volatile organic solvent in particular having an initial boiling point less than or equal to 250° C. measured at a standard atmospheric pressure of 101.3 kPa). Most preferably the composition is 100% UV radiation curable. A 100% radiation curable composition refers to a composition which is substantially free of water and volatile organic solvent which preferably have to be removed before complete curing is achieved. Substantially free of water and volatile organic solvent means that water and volatile organic solvent are not intentionally added to the composition, however the presence of low amounts of water and/or volatile organic solvent cannot be excluded since low amounts of water and/or volatile organic solvent may be present in raw materials and in additives that are added to the composition. As used herein, substantially free of water and volatile organic solvent (also referred to as in the substantial absence of water and volatile organic solvent) means that the composition contains less than 5 wt. % of water and volatile organic solvent, preferably less than 3 wt. % of water and volatile organic solvent, more preferably less than 1 wt. % of water and volatile organic solvent by weight of the solids content of the composition of the present invention. The present invention also relates to a 100% radiation curable composition comprising at least one compound (II) comprising at least two radical copolymerisable ethylenically unsaturated groups, wherein the composition comprises at least one aziridinyl functional compound (1) as described above and wherein the composition contains less than 5 wt. % of water and volatile organic solvent, preferably less than 3 wt. % of water and volatile organic solvent, more preferably less than 1 wt. % of water and volatile organic solvent by weight of the solids content of the composition of the present invention.

The radical copolymerisable ethylenically unsaturated groups of compound (II) are preferably (meth)acryloyl ester groups, (meth)acrylamide groups and any combination thereof. More preferably, the radical copolymerisable ethylenically unsaturated groups of compound (11) are (meth) acryloyl ester groups. Even more preferably, the radical copolymerisable ethylenically unsaturated groups of compound (II) are acryloyl ester groups.

The one or more compounds (II) in which the radical copolymerisable ethylenically unsaturated group are (meth) acryloyl ester groups may comprise at least one (meth) acrylated oligomer. The (meth)acrylated oligomers are typically composed of only a few monomer units such as a dimer, trimer, tetramer etc. The use of one or more (meth) acrylated polymers is possible as well.

Examples of suitable compounds (II) in which the radical copolymerisable ethylenically unsaturated group are (meth) acryloyl ester groups include those selected from the group consisting of polyester (meth)acrylates, polyether (meth) acrylates, epoxy (meth)acrylates, amino (meth)acrylates, polycarbonate (meth)acrylates, (poly)urethane (meth)acrylates, (meth)acrylated (meth)acrylics, or mixtures thereof. Preferred are polyester (meth)acrylates, polyether (meth) acrylates and/or epoxy (meth)acrylates. Most preferred are urethane (meth)acrylates, polyester (meth)acrylates and/or epoxy (meth)acrylates. By "(meth)acrylates" is meant to designate acrylates, methacrylates or mixtures thereof. Acrylates are generally preferred because of their higher UV reactivity.

Polyester (meth)acrylate oligomers are well known. These (meth)acrylated polyesters can be obtained by reacting a hydroxyl group-containing polyester backbone with (meth)acrylic acid, or by reacting a carboxyl group-containing polyester backbone with a hydroxyalkyl (meth)acrylate such as for example 2-hydroxyethyl acrylate, 2- or 3-hydroxypropyl acrylate, etc. or with glycidyl (meth)acrylate. The polyester backbone can be obtained in a conventional manner by polycondensation of at least one polyhydroxy alcohol, such as ethylene glycol, propylene glycol, butanediol, neopentyl glycol, hexanediol, trimethylolpropane, bisphenol A, pentaerythritol, etc, and/or the ethoxylates and/or propoxylates thereof, with at least one polycarboxylic acid or anhydride thereof such as adipic acid, phthalic acid, isophthalic acid, terephthalic acid, trimellitic acid, etc. By using unsaturated compounds for the polyester synthesis, such as for example fumaric acid, maleic acid, itaconic acid, etc., polyesters bearing both (meth)acrylic and ethylenic unsaturations in the polymer chain, can be obtained. In addition polylactones and/or polylactides can be used as polyester backbone. For example poly(e-caprolactone), polylactide and/or poly(lactide, caprolactone) can be obtained by ring-opening polymerization of e-caprolactone and/or lactide optionally in the presence of one or more polyhydroxy alcohols. Examples of suitable polyester (meth)acrylates include AgiSyn™ 705, AgiSyn™ 707 AgiSyn™716, AgiSyn™720, AgiSyn™730, AgiSyn™740, NeoRad™P-11, NeoRad™P50, NeoRad™P-56 available from DSM.

Polyether (meth)acrylate oligomers can be prepared by esterification of hydroxyfunctional polyethers with (meth) acrylic acid. Hydroxyfunctional polyethers can be obtained by ring-opening homo- or copolymerization of cyclic ethers such as tetrahydrofuran, ethylene oxide and/or propylene oxide, or can be prepared by reacting polyhydroxy alcohols with ethylene and/or propylene oxide.

Polycarbonate (meth)acrylate oligomers are also well known. They can be prepared by esterification of hydroxyfunctional polycarbonates with (meth)acrylic acid.

(Poly)urethane (meth)acrylate oligomers can be prepared by reacting a di- and/or polyisocyanate, such as hexamethylene-diisocyanate, isophorone-diisocyanate, toluene-diisocyanate, with hydroxyl functional (meth)acrylate. Use can be made exclusively of hydroxyl functional (meth)acrylates such as those mentioned above, but in order to extend the chain, mono- or polyhydroxy alcohols can also be added, such as those mentioned above for the synthesis of polyesters polyesters, polyethers or polycarbonates containing hydroxyl groups. Examples of suitable urethane (meth) acrylates include AgiSyn™ 230T1, AgiSyn™ 230A2, AgiSyn™ 230S1-B85, NeoRad™ U-10-15T, NeoRad™ U-20-12H, NeoRad™ all available from DSM. An example of a suitable aromatic urethane (meth)acrylates: AgiSyn™ 670T1, NeoRad™ U60, NeoRad™ U-61, all available from DSM.

By epoxy (meth)acrylate oligomers is meant to designate the (meth)acrylic esters of epoxides, preferably polyepoxides, i.e. compounds comprising at least one, preferably at least two epoxide functions. Epoxy (meth)acrylate oligomers are generally obtained from the esterification reaction of (meth)acrylic acid with epoxides. The epoxides are generally chosen from epoxidized olefins, glycidyl esters of saturated or unsaturated carboxylic acids, glycidyl ethers of aromatic or aliphatic alcohols or polyols and from cycloaliphatic polyepoxides. Preferred epoxides are diglycidylethers of aromatic and aliphatic diols and cycloaliphatic diepoxides such as diglycidyl ether of bisphenol-A, diglycidyl ether of bisphenol-F, diglycidylether of poly(ethylene oxide-co-propylene oxide), diglycidylether of polypropylene oxide, diglycidylether of hexanediol, diglycidylether of butanediol. Particularly preferred is diglycidyl ether of bisphenol-A. Also epoxidized natural oils or epoxidized phenol-formaldehyde copolymers can be used. Examples of natural oils include soybean oil, linseed oil, perilla oil, fish oil, dehydrated castor oil, tung oil, coconut oil, corn oil, cottonseed oil, olive oil, palm oil, palm kernel oil, peanut oil, sunflower oil, safflower oil, castor oil. Examples of suitable epoxy (meth)acrylates include AgiSyn™ 1010, AgiSyn™1030, AgiSyn™1050, AgiSyn™ 2020, AgiSyn™ 3050, AgiSyn™ 3051 all available from DSM.

(Meth)acrylated (meth)acrylic oligomers can be obtained by first preparing a (meth)acrylic copolymer by copolymerization of (meth)acrylate monomers such as butyl acrylate with monomers containing pendant carboxylic acid, anhydride, hydroxy, glycidyl or isocyanate groups and by then reacting this copolymer with a monomer comprising at least one (meth)acrylate functional group and at least one carboxylic acid, anhydride, hydroxyl, glycidyl or isocyanate reactive groups. For example, a glycidyl group-containing copolymer can first be prepared by copolymerizing functionalized monomers such as glycidyl (meth)acrylate with other (meth)acrylate monomers, the said glycidyl group-containing polymer being usually reacted in a second step with (meth)acrylic acid. When the functionalized monomers are (meth)acrylic acid, the carboxyl group-containing polymer is generally reacted in the second step with glycidyl (meth)acrylate. Examples of suitable (meth)acrylated (meth) acrylic are AgiSyn™ 9790, NeoRad™ A-20 all available from DSM.

Also amino (meth)acrylates can be added as such to the composition of the invention. Amino(meth)acrylates can be obtained by the addition reaction of a (meth)acrylate and an amine. Examples of suitable amino (meth)acrylates include AgiSyn™701, AgiSyn™701P, AgiSyn™ 703, AgiSyn™ 002, AgiSyn™003, NeoRad™ P-85, all available from DSM.

Compounds (II) in which the radical copolymerisable ethylenically unsaturated group are (meth)acryloyl ester groups typically are poly(meth)acrylates containing from 2 to 10 (meth)acryloyl groups per molecule. By "(meth) acryloyl groups" is meant acrylyol groups, methacryloyl groups or a mixture of both. Acryloyl groups are herein preferred.

Compounds (II) in which the radical copolymerisable ethylenically unsaturated group are (meth)acryloyl ester groups typically comprise from 2 to 6 and most typically from 2 to 4 (meth)acryloyl ester groups. Acryloyl ester groups are herein preferred.

Preferably compounds (II) have a number average molecular weight (Mn) of at least 300 Dalton and more preferably at least 500 Dalton. Often they have a Mn of at least 1,000 Dalton. Typically compounds (II) have a Mn of at most 20,000 Dalton, preferably at most 10,000 Dalton, more preferably at most 9,000 Dalton and even more preferably at most 8,000 Dalton. Number average molecular weights are herein determined by MALDI-ToF-MS.

The one or more compounds (II) may also comprise at least one reactive monomer or diluent as well known in the art. Often the one or more compounds (II) comprise at least one (trimethylolpropane)acrylated oligomer and at least one (meth)acrylated monomer. In embodiments, the (meth)acrylated monomers may be monofunctional, difunctional, or trifunctional, tetrafunctional, pentafunctional or hexafunctional (meth)acrylate monomers. Representative examples of such monomers include but are not limited to: (meth) acrylic acid, ethylene glycol di(meth)acrylate, ethoxylated bisphenol A di(meth)acrylate esters, isosorbide di(meth) acrylate, tris(2-hydroxyethyl) isocyanurate tri(meth)acrylate as well as the di(meth)acrylate, alkyl (such as isobornyl, isodecyl, isobutyl, n-butyl, t-buyl, methyl, ethyl, tetrahydrofurfuryl, cyclohexyl, n-hexyl, iso-octyl, 2-ethylhexyl, n-lauryl, octyl or decyl) or hydroxy alkyl (such as 2-hydroxyethyl and hydroxy propyl) esters of acrylic acid or methacrylic acid, phenoxyethyl(meth)acrylate, nonylphenolethoxylate mono(meth)acrylate, 2-(-2-ethoxyethoxy)ethyl(meth)acrylate, 2-butoxyethyl(meth)acrylate, butyleneglycol di(meth) acrylate and tri(meth)acrylate, tripropyleneglycol di (meth) acrylate, dipropyleneglycol di (meth)acrylate, 1,6-hexanediol di(meth)acrylate, ethoxylated and/or propoxylated hexanediol di(meth)acrylate, tricyclodecanedi (meth)acrylate, tricyclodecanedimethanol di(meth)acrylate, di-pentaerythrytol hexa acrylate (DPHA), propylene glycol di(meth)acrylate, neopentyl glycol di(meth)acrylate, ethoxylated and/or propoxylated neopentylglycol di(meth) acrylate, hexamethylene glycol di(meth)acrylate, 4,4'-bis(2-acryloyloxyethoxy)diphenylpropane, di-trimethylolpropane tetra(meth)acrylate and the ethoxylated or/and propoxylated derivatives thereof, phenylglycidylether(meth)acrylate, the (meth)acrylates obtained from the esterification with (meth) acrylic acid of aliphatic glycidyl ethers, glycerol triacrylate and their (poly)ethoxylated and/or (poly)propoxylated equivalents and any mixture thereof and any combination thereof.

In a preferred embodiment, the one or more compounds (II) further comprise at least one reactive monomer or diluent preferably selected from the group consisting of trimethylolpropane tri(meth)acrylate and their (poly)ethoxylated and/or (poly)propoxylated equivalents, di-trimethylolpropane tetra(meth)acrylate and their (poly)ethoxylated and/or (poly)propoxylated equivalents, glycerol tri(meth) acrylate and their (poly)ethoxylated and/or (poly) propoxylated equivalents and any mixture thereof. In another preferred embodiment, the one or more compounds (II) are preferably selected from the group consisting of trimethylolpropane tri(meth)acrylate and their (poly)ethoxylated and/or (poly)propoxylated equivalents, di-trimethylolpropane tetra(meth)acrylate and their (poly)ethoxylated and/or (poly)propoxylated equivalents, glycerol tri(meth) acrylate and their (poly)ethoxylated and/or (poly) propoxylated equivalents and any mixture thereof.

The radical copolymerisable ethylenically unsaturated group of compound (II) are preferably acryloyl ester groups and compound (I) present in the composition of the invention preferably contains acryloyl ester groups.

The amount of compound (I) in the composition of the invention is preferably at least 2 wt. %, more preferably at least 5 wt. %, relative to the total amount of the composition. The amount of compound (1) in the composition of the invention is preferably at most 40 wt. %, more preferably at most 30 wt. %, even more preferably at most 20 wt. %, relative to the total amount of the composition. the amount of compound (II) is at least 60 wt. %, preferably at least 70 wt. %, more preferably at least 80 wt. %, and at most 90 wt. %, preferably at most 95 wt. % and more preferably at most 98 wt. %, relative to the total amount of the composition.

The molar ratio of aziridinyl groups with the following structural formula

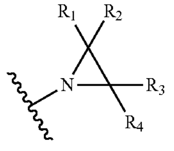

to ethylenically unsaturated bonds in said compound (I) is preferably in the range of from 1:5 to 1:1, more preferably from 1:3 to 1:1.

The ethylenically unsaturated bond concentration of the curable composition is preferably in the range from 0.5 to 6 milliequivalents per g of the curable composition. As used herein, the amount of C═C bonds present in the composition is determined by adding up all radiation-curable C═C functionality from the components used to prepare the composition.

The composition of the present invention is preferably used for coating a substrate or for printing an image on a substrate. The present invention therefore further relates to a coating composition or to an ink composition comprising the radiation-curable composition as described above. The substrate to which the composition is applied preferably contains wood, paper, metal, plastic, textile, leather, glass, concrete, packaging film or any combination thereof. More preferably, the substrate is selected from the group consisting of wood, metal, plastic, linoleum, concrete, glass and any combination thereof. Even more preferably the substrate is a flexible plastic, preferably biaxially oriented polypropylene, polyethylene and polyethylene terephthalate. The substrate to which the composition is applied can advantageously be used in food packaging.

Preferably, the composition of the invention is applied for an ink composition. The ink composition is preferably an UV inkjet ink composition, an offset ink composition or a flexo ink composition.

The invention is further defined by the set of exemplary embodiments as listed hereafter. Any one of the embodiments, aspects and preferred features or ranges as disclosed in this application may be combined in any combination, unless otherwise stated herein or if technically clearly not feasible to a skilled person.

[1]A compound (1) comprising at least one functional group A and at least one functional group B, wherein the functional groups A has structural formula A:

(A)

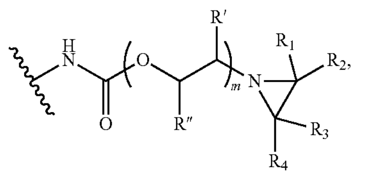

wherein $R_1$ is H, $R_2$, $R_3$ and $R_4$ are independently chosen from H, methyl or ethyl, m is 1 to 6, R' and R" are according to (1) or (2):

(1) R'=H or an aliphatic hydrocarbon group containing from 1 to 14 carbon atoms, and R"=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C═O)—R''', $CH_2$—O—R'''', or $CH_2$—(OCR'''''HCR'''''H)$_n$—OR'''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R''''' independently being H or an aliphatic hydrocarbon group containing from 1 to 14 carbon atoms and R'''''' being an aliphatic hydrocarbon group containing from 1 to 4 carbon atoms, (2) R' and R" form together a saturated cycloaliphatic hydrocarbon group containing from 5 to 8 carbon atoms; and the functional groups B has structural formula B:

(B)

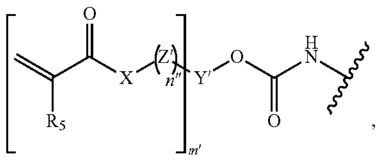

$R_5$ is H or methyl,

X is O or NH,

Z' is a polyalkoxy group or an omega-alkoxy polycaprolacton group,

Y' is a collection of atoms covalently connected in linear or branched configuration which collection of atoms consists of i) carbon and hydrogen atoms, ii) carbon, hydrogen and oxygen atoms, iii) carbon, hydrogen and nitrogen atoms, or iv) carbon, hydrogen, oxygen and nitrogen atoms, n" is 0 or 1, and m' is an integer from 1 to 6;

with the proviso that the summed amount of the number of functional groups A and the number of functional groups B in compound (I) is from 2 to 13; and the compound has a molecular weight in the range from 600 Daltons to 10000 Dalton.

[2] The compound of embodiment [1], wherein $R_2$ is H, $R_3$ is $C_2H_5$ and $R_4$ is H.

[3] The compound of embodiment [1], characterized in that $R_2$ is H, $R_3$ is $CH_3$ and $R_4$ is H.

[4] The compound of embodiment [1], wherein $R_2$ is H, $R_3$ is $CH_3$ and $R_4$ is $CH_3$.

[5] The compound according to any of embodiments [1] to [4], wherein m is 1.

[6] The compound according to any of embodiments [1] to [5], wherein

R' and R" are according to (1) or (2):

(1) R'=H or an alkyl group containing from 1 to 2 carbon atoms;

R"=H, an aliphatic hydrocarbon group containing from 1 to 4 carbon atoms, CH2-O—(C═O)—R''', CH2-O—R'''', or CH2-(OCR'''''HCR'''''H)n-OR'''''', whereby R''' is an alkyl group containing from 1 to 14 carbon atoms and R'''' is an alkyl group containing from 1 to 14 carbon atoms, n being from 1 to 35, R''''' independently being H or a methyl group and R'''''' being an alkyl group containing from 1 to 4 carbon atoms;

(2) R' and R" form together a saturated cycloaliphatic hydrocarbon group containing from 5 to 8 carbon atoms.

[7] The compound according to any of embodiments [1] to [6], wherein

R' is H and R"=an alkyl group containing from 1 to 4 carbon atoms, more preferably R" is methyl.

[8] The compound according to any of embodiments [1] to [7], wherein $R_5$ is H.

[9] The compound according to any of embodiments [1] to [8], wherein X is O.

[10] The compound according to any of embodiments [1] to [9], wherein Z' is a polyalkoxy group having from 1 to 10 alkoxy repeating units, preferably from 3 to 6 alkoxy repeating units and the alkoxy repeating units are preferably ethoxy, propoxy or butoxy repeating units.

[11] The compound according to any of embodiments [1] to [10], wherein Z' is an omega-alkoxy polycaprolacton group preferably having from 2 to 6 repeating units, preferably from 3 to 6 repeating units.

[12] The compound according to any of embodiments [1] to [11], wherein the compound has structural formula $(A)_p$-W—$(B)_q$, wherein p and q are independently an integer of at least 1, p+q is an integer from 2 to 13 and W consists of a collection of atoms covalently connected in a linear or branched configuration which collection of atoms consists of: i) carbon and hydrogen atoms, ii) carbon, hydrogen and oxygen atoms, iii) carbon, hydrogen and nitrogen atoms, iv) carbon, hydrogen, oxygen and nitrogen atoms, or v) carbon, hydrogen and sulphur atoms.

[13] The compound according to any of embodiments [1] to [11], wherein the compound has structural formula $(A)_p$-W—$(B)_q$, p and q are independently an integer of at least 1, p+q is an integer from 2 to 13 and W consists of a collection of atoms covalently connected in a linear or branched configuration which collection of atoms consists of: i) carbon and hydrogen atoms, ii) carbon, hydrogen and oxygen atoms, iii) carbon, hydrogen and nitrogen atoms, or iv) carbon, hydrogen, oxygen and nitrogen atoms.

[14] The compound according to embodiment [11] or [12], wherein m' in structural formula (B) is 1 and q is 1 or 2 and p is 1 or 2.

[15] The compound according to embodiment [11] or [12], wherein m' in structural formula (B) is 1 and q is 1 and p is 2.

[16] The compound according to embodiment [11] or [12], wherein m' in structural formula (B) is from 2 to 6 and q is 1 and p is 1 or 2, preferably p is 1.

[17] The compound according to any of embodiments [11] to [16], wherein W consists of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof

[18] The compound according to any of embodiments [11] to [16], wherein W consists of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, urethane functionality, urea functionality, biuret functionality and any combination thereof.

[19] The compound according to any of embodiments [11] to [16], wherein W consists of at least one aliphatic hydrocarbon functionality and/or at least one cycloaliphatic hydrocarbon functionality and optionally at least one aromatic hydrocarbon functionality and optionally an isocyanurate functionality or an iminooxadiazindione functionality.

[20] The compound according to any of embodiments [11] to [16], wherein W contains an isocyanurate functionality or an iminooxadiazindione functionality

[21] The compound according to any of embodiments [11] to [16], wherein W consists of at least one aliphatic hydrocarbon functionality and/or at least one cycloaliphatic hydrocarbon functionality, and an isocyanurate functionality or an iminooxadiazindione functionality.

[22] The compound according to any of embodiments [11] to [21], wherein W inintroduced into compound (1) by using as raw material compound W' being at least one polyisocyanate and/or at least one isocyanate terminated polyurethane.

[23] The compound according to embodiment [22], wherein the polyisocyanate has aliphatic reactivity and is preferably 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, p-tetra-methylxylene diisocyanate (p-TMXDI) and its meta isomer, and/or higher molecular weight variants like for example their isocyanurates or iminooxadiazindiones or allophanates or uretdiones.

[24] The compound according to embodiment [22], wherein the polyisocyanate has aliphatic reactivity and is preferably 4,4'-dicyclohexyl methane diisocyanate H12MDI, m-TMXDI, an isocyanurate or iminooxadiazindione or allophanate or uretdione of 1,6-hexamethylene diisocyanate and/or an isocyanurate of 1,5-pentamethylene diisocyanate.

[25] The compound according to any of embodiments [1] to [24], wherein the molecular weight is in the range of from 600 Daltons to 5000 Daltons, preferably at least 700 Daltons, more preferably the molecular weight is at least 800 Daltons and preferably at most 3800 Daltons, more preferably at most 3600 Daltons, more preferably at most 3000 Daltons, more preferably at most 1600 Daltons.

[26] Use of the compound as claimed in any one of the embodiments [1] to [25] as adhesion promotor or reactive diluent in free radical curable compositions, preferably in 100% UV radiation curable compositions).

[27]A 100% radiation curable composition comprising at least one aziridinyl functional compound (I) of any of the embodiments [1] to [25], and at least one compound (II) comprising at least two radical copolymerisable ethylenically unsaturated groups.

[28] The composition according to embodiment [27], wherein the summed amount of the number of functional groups A and the number of functional groups B in compound (I) is preferably from 3 to 10, more preferably the summed amount of the number of functional groups A and the number of functional groups B in compound (1) is from 3 to 7, even more preferably is 3.

[29] The composition according to embodiment [27] or [28], wherein the radical copolymerisable ethylenically unsaturated groups of compound (1) are (meth)acryloyl ester groups, (meth)acrylamide groups and any combination thereof.

[30] The composition according to any of embodiments [27] to [29], wherein the radical copolymerisable ethylenically unsaturated groups of compound (I) are (meth)acryloyl ester groups.

[31] The composition according to any one of embodiments [27] to [30], wherein compound (II) comprises at least one of urethane(meth)acrylate, at least one of polyester (meth) acrylate, at least one of epoxy(meth)acrylate, at least one of (meth)acrylated monomer or any mixture thereof.

[32] The composition according to any one of embodiments [27] to [31], wherein compound (11) comprises a (meth) acrylated monomer selected from the group consisting of trimethylolpropane tri(meth)acrylate and their (poly)ethoxylated and/or (poly)propoxylated equivalents, di-trimethylolpropane tetra(meth)acrylate and their (poly)ethoxylated and/or (poly)propoxylated equivalents, glycerol tri(meth) acrylate and their (poly)ethoxylated and/or (poly) propoxylated equivalents and any mixture thereof.

[33] The composition according to any one of embodiments [27] to [31], wherein compound (II) is a (meth)acrylated monomer selected from the group consisting of trimethylolpropane tri(meth)acrylate and their (poly)ethoxylated and/or (poly)propoxylated equivalents, di-trimethylolpropane tetra(meth)acrylate and their (poly)ethoxylated and/or (poly) propoxylated equivalents, glycerol tri(meth)acrylate and their (poly)ethoxylated and/or (poly)propoxylated equivalents and any mixture thereof.

[34] The composition according to any one of embodiments [27] to [33], wherein the amount of compound (I) is least 2 wt. %, preferably at least 5 wt. %, and at most 40 wt. %, preferably at most 30 wt. %, more preferably at most 20 wt. %, relative to the total amount of the composition.

[35] The composition according to any one of embodiments [27] to [34], wherein the amount of compound (II) is at least 60 wt. %, preferably at least 70 wt. %, more preferably at least 80 wt. %, and at most 90 wt. %, preferably at most 95 wt. % and more preferably at most 98 wt. %, relative to the total amount of the composition.

[36] The composition according to any one of embodiments [27] to [35], wherein the molar ratio of aziridinyl groups with the following structural formula

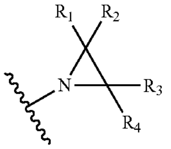

to ethylenically unsaturated bonds in said compound (1) is in the range of from 1:5 to 1:1, more preferably from 1:3 to 1:1.

[37] The composition according to any one of embodiments [27] to [36], wherein the ethylenically unsaturated bond concentration of the curable composition is in the range from 0.5 to 6 milliequivalents per g of the curable composition.

[38] The composition according to any one of embodiments [27] to [37], wherein the composition is UV-curable.

[39] The composition according to embodiment [38], wherein the composition comprises a photo-initiator.

[40] An ink composition comprising the composition of any one of embodiments [39] to [36].

[41]A substrate having a coating obtained by (i) applying the composition according to any one embodiments [27] to [39] to a substrate and (ii) curing the composition.

[42] The substrate according to embodiment [41], wherein the substrate is a flexible plastic, preferably biaxially oriented polypropylene, polyethylene and polyethylene terephthalate.

[43]A food packaging comprising a substrate according to embodiment [42].

The present invention is now illustrated by reference to the following examples. Unless otherwise specified, all parts, percentages and ratios are on a weight basis.

pH Measurement

The pH of a sample is determined based on the ISO 976:2013 standard. Samples are measured at 23° C. using a Metrohm 691 pH-meter equipped with combined glass electrode and PT-1000 temperature sensor. The pH-meter is calibrated using buffer solutions of pH 7.00 and 9.21 prior to use.

NCO Determination

The NCO content of a sample is determined based on the ASTM D2572-19 standard. In the procedure, the sample is reacted with excess n-dibutylamine. The excess of n-dibutylamine is subsequently back-titrated with standard 1 N hydrochloric acid (HCl). The difference in titration volume between the sample and a blank is the measure of the isocyanate content on solids, according to the following formula: $\% NCO_{solids}=[(Vb-Vm)*N*4.2]/(A*s/100)$, where $\% NCO_{solids}$ is the isocyanate content on solids, Vb is the volume of HCl used in the blank, Vm is the volume of HCl used in the sample, N is the normality of the HCl solution, A is the sample weight in grams and s is the solids content of the sample in %. Measurements are performed in duplicate using a potentiometric endpoint on a Metrohm 702SM Titrino titrator (accepting the measurement if the difference between duplicates is $<0.1\%_{NCO}$).

AV Determination

The acid value on solid material (AV) of a sample is determined based on the ASTM D1639-90(1996)e1 standard. In the procedure, the sample, dissolved in a good solvent, is titrated with alcoholic potassium hydroxide solution of a known concentration (KOH). The difference in titration volume between the sample and a blank is the measure of the acid value on solids, according to the following formula: $AV=[(Vblank-Vsample)*N_{KOH}*56.1]/(W*S/100)$, where AV is acid number on solids in mg KOH/g solid material, Vblank is the volume of KOH solution used in the blank, Vsample is the volume of KOH solution used in the sample, $N_{KOH}$ is the normality of the KOH solution, W is the sample weight in grams and S is the solids content of the sample in %. Measurements are performed in duplicate using a potentiometric endpoint on a Metrohm 702SM Titrino titrator (accepting the measurement if the difference between duplicates is <0.1 mg KOH/g solid material).

Low Molecular Weight Fraction by LC-MS

LC system: Agilent 1290 Infinity 11; Detector #1: Agilent 1290 Infinity II PDA; Detector #2: Agilent iFunnel 6550 Q-TOF-MS.

LC-MS analysis for the low molecular weight fraction was performed using the following procedure. A solution of ~100 mg/kg of material was prepared gravimetrically in methanol and stirred. 0.5 μl of this solution was injected into a UPLC equipped with ESI-TOF-MS detection. The column used was a 100×2.1 mm, 1.8 um, Waters HSS T3 C18 operated at 40° C. Flow rate was 0.5 $ml \cdot min^{-1}$. Solvents used were 10 mM $NH_4CH_3COO$ in water set to pH 9.0 with $NH_3$ (Eluent A), Acetonitrile (B) and THF (C). Two binary gradients were applied from 80/20 A/B to 1/99 A/B in 10 minutes and from 1/99 A/B to 1/49/50 A/B/C in 5 minutes, after which starting conditions are applied (80/20 A/B). Assuming linear MS response of all components over all response ranges and an equal ionization efficiency for all components, Total Ion Current signals were integrated. In case of coelution extracted ion chromatograms of that particular species were integrated. Dividing the integrated signal of a particular low-molecular weight peak by the total integrated sample signal yields the fraction of that low molecular weight species.

Maldi-Tof-Ms

All MALDI-ToF-MS spectra were acquired using a Bruker Ultraflextreme MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterisation, code MC-MS-05). The laser energy was 20%. The samples were dissolved in THF at approx. 50 mg/mL. The matrix used was: DCTB (trans-2-[3-(4-tert-Butylphenyl)-2-methyl-2-propenylidene]malononitrile), CAS Number 300364-84-5. The matrix solution was prepared by dissolving 20 mg in 1 mL of THF.

Sodium iodide was used as salt (NaI, CAS Number 7681-82-5); 10 mg was dissolved in 1 ml THF with a drop of MeOH added. Ratio sample:matrix:salt=10:200:10 (μl), after mixing, 0.5 μL was spot on MALDI plate and allowed to air-dry. The peaks measured in the MALDI spectrum are sodium adducts of aziridinyl functional compounds (I), and in the context of this specification the molecular weight (MW) of the aziridinyl functional compound (I) corresponds to MW=Obs. $[M+M_{cation}]-M_{cation}$, where Obs. $[M+M_{cation}]$ is the MALDI-TOF MS peak and $M_{cation}$ is the exact mass of the cation used for making the adduct (in this case sodium with $M_{cation}$=23.0 Da). Aziridinyl functional compounds (1) can be identified by comparing the MW with the exact molecular mass (i.e. the sum of the—non-isotopically averaged—atomic masses of its constituent atoms) of a theoretical structure, using a maximum deviation of 0.6 Da.

Genotoxicity Testing

Genotoxicity of was evaluated by the ToxTracker® assay (Toxys, Leiden, the Netherlands). The ToxTracker assay is a panel of several validated Green Fluorescent Protein (GFP)-based mouse embryonic stem (mES) reporter cell lines that can be used to identify the biological reactivity and potential carcinogenic properties of newly developed compounds in a single test. This methodology uses a two step-approach. In the first step a dose range finding was performed using wild-type mES cells (strain B4418). 20 different concentrations for each compound was tested, starting at 10 mM in DMSO as highest concentration and nineteen consecutive 2-fold dilutions.

Next, genotoxicity of was evaluated using specific genes linked to reporter genes for the detection of DNA damage; i.e. Bscl2 (as elucidated by U.S. Pat. No. 9,695,481B2 and EP2616484B1) and Rtkn (Hendriks et. al. Toxicol. Sci. 2015, 150, 190-203) biomarkers. Genotoxicity was evaluated at 10, 25 and 50% cytotoxicity in absence and presence of rat S9 liver extract-based metabolizing systems (aroclor1254-induced rats, Moltox, Boone, NC, USA). The independent cell lines were seeded in 96-well cell culture plates, 24 h after seeding the cells in the 96-well plates, fresh ES cell medium containing the diluted test substance was added to the cells. For each tested compound, five concentrations are tested in 2-fold dilutions. The highest sample concentration will induce significant cytotoxicity (50-70%). In case of no or low cytotoxicity, 10 mM or the maximum soluble mixture concentration is used as maximum test concentration. Cytotoxicity is determined by cell count after 24 h exposure using a Guava easyCyte 10HT flow cytometer (Millipore).

GFP reporter induction is always compared to a vehicle control treatment. DMSO concentration is similar in all wells for a particular compound and never exceeds 1%. All compounds were tested in at least three completely independent repeat experiments. Positive reference treatment with cisplatin (DNA damage) were included in all experiments. Metabolic was evaluated by addition of S9 liver extract. Cells are exposed to five concentrations of the test compound in the presence of S9 and required co-factors (RegenSysA+B, Moltox, Boone, NC, USA) for 3 h. After washing, cells are incubated for 24 h in fresh ES cell medium. Induction of the GFP reporters is determined after 24 h exposure using a Guava easyCyte 10HT flow cytometer (Millipore). Only GFP expression in intact single cells is determined. Mean GFP fluorescence and cell concentrations in each well is measured, which is used for cytotoxicity assessment. Data was analyzed using ToxPlot software (Toxys, Leiden, the Netherlands). The induction levels reported are at compound concentrations that induce 10%, 25% and 50% cytotoxicity after 3 h exposure in the presence of S9 rat liver extract and 24 h recovery or alternatively after 24 h exposure when not in the presence of S9 rat liver extract.

A positive induction level of the biomarkers is defined as equal to or higher than a 2-fold induction at at least one of 10, 25 and 50% cytotoxicity in the absence or presence of the metabolizing system rat S9 liver extract; a weakly positive induction as higher than 1.5-fold and lower than 2-fold induction at at least one of 10, 25 and 50% cytotoxicity (but lower than 2-fold at 10, 25 and 50% cytotoxicity) in the absence or presence of the metabolizing system rat S9 liver extract and a negative as lower than or equal to a 1.5-fold induction at 10, 25 and 50% cytotoxicity in the absence and presence of rat S9 liver extract-based metabolizing systems.

Adhesion to Flexible Plastic Substrates

Table 1 lists the tested substrates.

TABLE 1

Overview of the tested flexible plastic substrates.

| Product | Producer | Description | Surface tension untreated (dyne/cm) | Surface tension Corona treated (dyne/cm) |
|---|---|---|---|---|
| Label-Lyte 50LL210 | Jindal | Plain BOPP | 38 | 38 |
| Mylar A | DuPont | Plain PET | 42 | >60 |
| | NPC | Plain PET | 48 | >60 |
| | EMTCO | Plain PVC | <34 | <34 |

In case of Corona treatment the total amount of energy applied is 0.35 kW. The surface tension of the foils was measured with Arcotest BLUE surface tension pens.

Ink Application

The inks were printed in duplo on the (treated) foils by means of an IGT C1-5 test-printer; rubber blanket and 300N print force. Aim of printed foils was to have a coat weights between 1.0 and 1.6 g/$m^2$ and a colour density between 1.3 and 1.6, determined with an X-Rite DensiEye 700.

Curing Conditions

The printed inks were cured by means of UV dryer, medium pressure Hg lamp, 5 passes. Total UV curing energy, dose & intensity, are measured with an EIT UV Power Puck II having 4 UV light sensitive cells (Table 2).

TABLE 2

Intensity UV lamps used.

| UV detection cell | UV dose [mJ/cm2] | UV intensity [mW/cm2] |
|---|---|---|
| UVA | 650 | 180 |
| UVB | 535 | 153 |

TABLE 2-continued

| Intensity UV lamps used. | | |
|---|---|---|
| UV detection cell | UV dose [mJ/cm2] | UV intensity [mW/cm2] |
| UVC | 165 | 49 |
| UVV | 860 | 240 |

Ink Adhesion Test

Ink adhesion was tested by applying 5 cm long strips of 3M Scotch 600 tape (4.4N/cm adhesion to steel) and TESA 4124 tape (3.2N/cm adhesion to steel) on the flexible plastic substrate whilst being pressed thoroughly in place by hand to avoid any air bubbles. The adhesive tapes were then removed in a shocking backwards motion at an angle of approximately 60°. Adhesion was determined in %, which stands for amount of ink that is still present on the substrate after removal of the tape.

Synthesis of an Aziridine-Functional UV Curable Compound (I)

A reaction product with as main component mono-Az-di-Ac (this reaction product is further referred as mono-Az-di-Ac (1)) was prepared by placing 1-(2-methyl-aziridine-1-yl)-propan-2-ol (30.9 gram), 2-hydroxyethyl acrylate (62.2 gram), butylated hydroxytoluene (0.4 gram), phenothiazine (0.04 gram), and a reactive diluent (propoxylated glycerin triacrylate, GTPA, 98 gram) in a flask and heat this mixture to 50° C. under mild stirring. In a dropping funnel a mixture of GTPA (98 gram) and Desmodur® N3600 (160 gram) was placed. Next, bismuth neodecanoate (0.02 gram) was added to the reaction mixture and the mixture in the dropping funnel was added in 40 minutes. Next, GTPA (20 gram) was added to the reaction mixture and the temperature was raised to 70° C. The progress of the reaction was monitored by disappearance of the NCO groups by IR.

The calculated molecular weight of the theoretical main component was confirmed with Maldi-TOF-MS and is shown below:

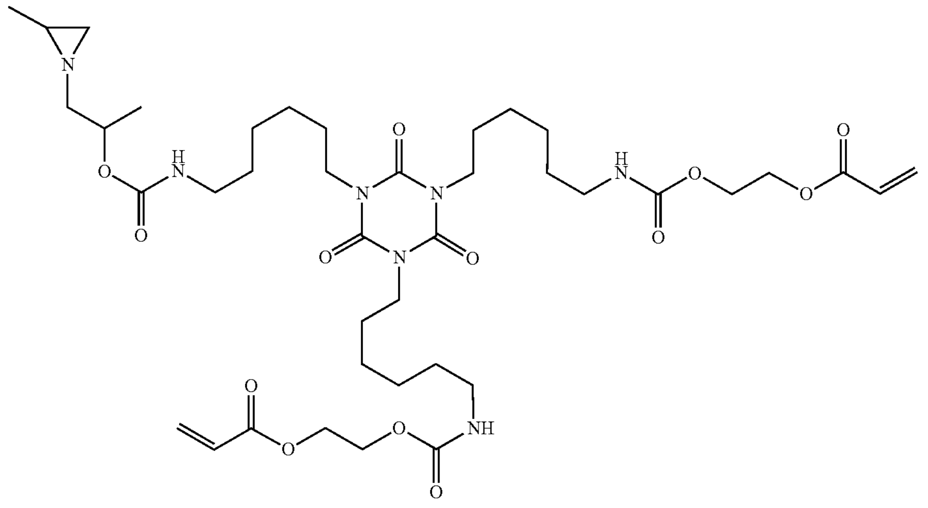 [SMILES: C=CC(=O)OCCOC(=O)NCCCCCCn1c(=O)n(CCCCCCNC(=O)OCCOC(=O)C=C)c(=O)n(CCCCCCNC(=O)OC(C)CN2CC2C)c1=O]

Examples and Comparative Experiments Compounds are named according to the chemical structure based on the molar ratio between acrylate bonds and aziridine groups. As an example, mono-Az-di-Ac denotes a compound having one aziridine (Az) group and two acrylate (Ac) groups. Agisyn 2836 is ethoxylated (3) trimethylolpropane triacrylate (CAS Nr. 28961-43-5), Agisyn 2837 is propoxylated (3) glyceryl triacrylate (CAS Nr. 52408-84-1). Agisyn 230A2 is an aliphatic urethane acrylic oligomer available from DSM. Agisyn 2816 is 1,6-hexanediol diacrylate (CAS Nr. 13048-33-4). Agisyn 2824 is propoxylated pentaerythritol triacrylate (CAS Nr. 145611-81-0). Agisyn 2858 is ethoxylated (9) trimethylolpropane triacrylate (CAS Nr. 28961-43-5) Desmodur® N3600 is obtained from Covestro. n-butylglycidyl ether (CAS Nr. 2426-08-6) and potassium carbonate (CAS No. 584-08-7) was obtained from Alfa Aesar (a division of Thermo Fisher Scientific). 2-Methylaziridine (propyleneimine, PI, CAS Nr. 75-55-8) was obtained from Menadiona S.L. (Palafolls, Spain). Butylated hydroxytoluene (CAS Nr. 128-37-0) and phenothiazine (CAS Nr. 92-84-2) were obtained from Sigma-Aldrich. Synthesis of 1-(2-methylaziridin-1-yl)propan-2-ol is described by S. Lesniak, M. Rachwalski, S. Jarzynski, E. Obijalska Tetrahedron Asymm. 2013, 24, 1336-1340.

Calcd. [M+Na+]=874.45 Da; Obs. [M+Na+]=874.32 Da.

Genotoxicity Test Results:

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration→ | 10 | 25 | 50 | 10 | 25 | 50 | 10 | 25 | 50 | 10 | 25 | 50 |
| Compound 1 | 1.0 | 1.2 | 1.3 | 1.0 | 1.0 | 1.0 | 1.2 | 1.2 | 1.2 | 1.0 | 1.0 | 1.0 |

The genotoxicity test results show that the reaction product obtained above is non-genotoxic.

Synthesis of an Aziridine-Functional UV Curable Compound (II)

A reaction product with as main component di-Az-mono-Ac (this reaction product is further referred as di-Az-mono-Ac (II)) was prepared according to the same procedure with adjusted amounts of 1-(2-methyl-aziridine-1-yl)-propan-2-ol and 2-hydroxyethyl acrylate.

The calculated molecular weight of the theoretical main component was confirmed with MALDI-TOF-MS and is shown below:

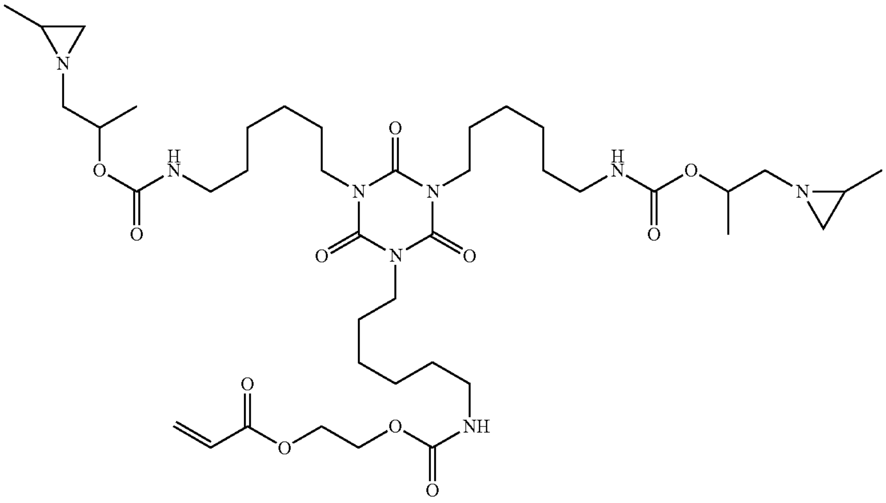

Calcd. [M+Na+]=873.51 Da; Obs. [M+Na+]=873.33 Da.

Synthesis of Tri-Ac Compound (Ill)

A compound tri-Ac has been prepared according to the same procedure using only Desmodur® N3600 and 2-hydroxyethyl acrylate and not using 1-(2-methyl-aziridine-1-yl)-propan-2-ol.

The calculated molecular weights of the theoretical main component was confirmed with MALDI-TOF-MS and is shown below:

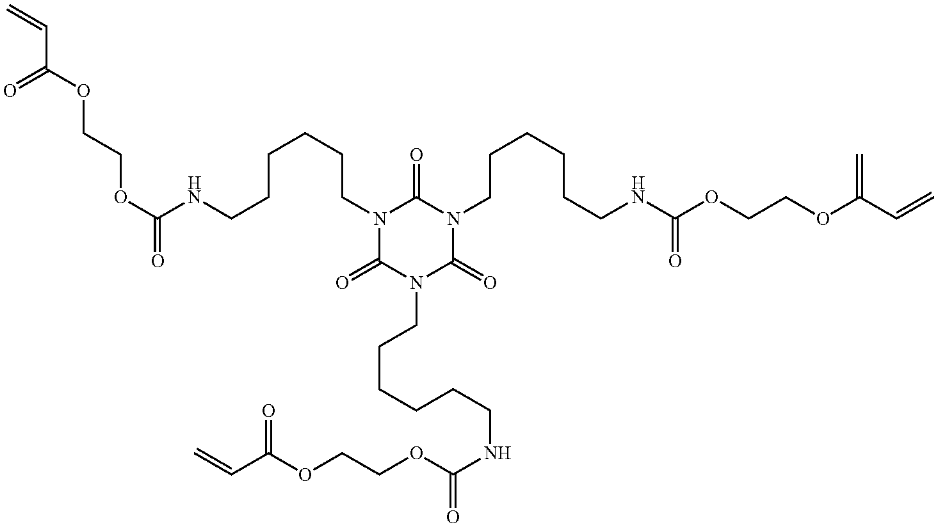 [SMILES: C=CC(=C)OCCOC(=O)NCCCCCCn1c(=O)n(CCCCCCNC(=O)OCCOC(=O)C=C)c(=O)n(CCCCCCNC(=O)OCCOC(=O)C=C)c1=O]

Calcd. [M+Na+]=875.40 Da; Obs. [M+Na+]=875.33 Da.

Ink Formulations

The composition of the pigment concentrates and initiator mix are listed in Table 3.

TABLE 3

Overview pigment concentrate and initiator mix.

| Pigment concentrate | Parts by weight | % by weight |
|---|---|---|
| Irgalite Rubine D4240 | 15.0 | 45.5 |
| AgiSyn 2836 | 8.2 | 24.8 |
| AgiSyn 2837 | 8.2 | 24.8 |

TABLE 3-continued

Overview pigment concentrate and initiator mix.

| | | |
|---|---|---|
| TegoAirex 920 | 0.1 | 0.3 |
| Solsperse 39000 | 1.5 | 4.6 |
| TOTAL | 33.0 | 100.0 |

TABLE 3-continued

Overview pigment concentrate and initiator mix.

| Initiator mix | Parts by weight | % by weight |
|---|---|---|
| Omnirad EHA | 4.0 | 40.0 |
| Omnirad TPO-L | 2.0 | 20.0 |
| Omnirad 819 | 2.0 | 20.0 |
| Omnirad 754 | 2.0 | 20.0 |
| TOTAL | 10.0 | 100.0 |

The formulations of the inks are given in Table 4 and the test results in Tables 5 and 6.

TABLE 4

Ink formulations of comparative experiment 1 (C1) and Examples 1 to 6

| Ink formulations | C1(comp) | 1 | 2 | 3 | 4 | 5 | 6 |
|---|---|---|---|---|---|---|---|
| Tri-Ac (III) | 25.0 | 16.7 | 8.3 | — | 16.7 | 8.3 | — |
| Mono-Az-di-Ac (I) | — | 15.4 | 30.9 | 46.3 | — | — | — |
| Di-Az-mono-Ac (II) | — | — | — | — | 8.3 | 16.7 | 25.0 |
| AgiSyn 2837 | 21.3 | 14.2 | 7.1 | | 21.3 | 21.3 | 21.3 |
| AgiSyn 2836 | 10.7 | 10.7 | 10.7 | 10.7 | 10.7 | 10.7 | 10.7 |
| Pigment concentrate | 33.0 | 33.0 | 33.0 | 33.0 | 33.0 | 33.0 | 33.0 |
| Initiator mix | 10.0 | 10.0 | 10.0 | 10.0 | 10.0 | 10.0 | 10.0 |
| TOTAL parts by weight | 100.0 | 100.0 | 100.0 | 100.0 | 100.0 | 100.0 | 100.0 |
| TOTAL AZIRIDINE CONTENT (mol/kg) | 0.000 | 0.088 | 0.177 | 0.265 | 0.174 | 0.351 | 0.525 |

Adhesion Results

The adhesion of Comparative Experiment C1 and Examples 1 to 6 on corona treated foils are shown in Table 5, the adhesion to untreated foils is shown in Table 6. In both test series two tapes are used to assess the adhesion.

TABLE 5

The adhesion of Comp Ex 1 and Ex 1-6 to corona treated foils.

| | C1(comp) | 1 | 2 | 3 | 4 | 5 | 6 |
|---|---|---|---|---|---|---|---|
| TOTAL AZIRIDINE CONTENT (mol/kg) | 0.000 | 0.088 | 0.177 | 0.265 | 0.174 | 0.351 | 0.525 |
| Plain BOPP [Jindal] | | | | | | | |
| 3M Scotch 600 | 0 | 100 | 100 | 100 | 100 | 100 | 100 |
| TESA 4124 | 35 | 100 | 100 | 100 | 100 | 100 | 100 |
| Plain PET [DuPont] | | | | | | | |
| 3M Scotch 600 | 0 | 100 | 100 | 100 | 100 | 100 | 100 |
| TESA 4124 | 0 | 100 | 100 | 100 | 100 | 100 | 100 |
| Plain PET [NPC] | | | | | | | |
| 3M Scotch 600 | 0 | 100 | 75 | 97.5 | 55 | 100 | 100 |
| TESA 4124 | 0 | 100 | 75 | 100 | 80 | 100 | 100 |
| Plain PVC [EMTCO] | | | | | | | |
| 3M Scotch 600 | 25 | 70 | 75 | 70 | 75 | 95 | 100 |
| TESA 4124 | 55 | 80 | 97.5 | 97.5 | 95 | 100 | 100 |

TABLE 6

The adhesion of Comp Ex 1 and Ex 1-6 to untreated foils.

| | C1(comp) | 1 | 2 | 3 | 4 | 5 | 6 |
|---|---|---|---|---|---|---|---|
| TOTAL AZIRIDINE CONTENT (mol/kg) | 0.000 | 0.088 | 0.177 | 0.265 | 0.174 | 0.351 | 0.525 |
| Plain BOPP [Jindal] | | | | | | | |
| 3M Scotch 600 | 0 | 100 | 100 | 100 | 100 | 100 | 100 |
| TESA 4124 | 100 | 100 | 100 | 100 | 100 | 100 | 100 |
| Plain PET [DuPont] | | | | | | | |
| 3M Scotch 600 | 0 | 75 | 90 | 97.5 | 100 | 100 | 95 |
| TESA 4124 | 0 | 75 | 100 | 97.5 | 100 | 100 | 97.5 |
| Plain PET [NPC] | | | | | | | |
| 3M Scotch 600 | 0 | 10 | 75 | 15 | 25 | 65 | 10 |
| TESA 4124 | 0 | 10 | 70 | 60 | 60 | 87.5 | 30 |

TABLE 6-continued

The adhesion of Comp Ex 1 and Ex 1-6 to untreated foils.

| | C1(comp) | 1 | 2 | 3 | 4 | 5 | 6 |
|---|---|---|---|---|---|---|---|
| Plain PVC [EMTCO] | | | | | | | |
| 3M Scotch 600 | 35 | 50 | 65 | 75 | 60 | 92.5 | 85 |
| TESA 4124 | 50 | 75 | 75 | 95 | 85 | 100 | 100 |

Tables 5 and 6 show that the UV-curable compositions that contain aziridine groups provide superior adhesion to corona treated and untreated flexible plastic foils compared to the UV-curable composition that does not contain aziridine groups. The results also show that the aziridine groups are essential to obtain good adhesion (example C1 does not provide good adhesion).

Adhesion to Rigid Plastic Substrates

The polypropylene PP used was supplied by Simona and has a surface tension of <34 mNm before corona treatment and >60 mN/m after treatment. In case of corona treatment the total amount of energy applied is 1.0 kW. The surface tension of the foils was measured with Arcotest BLUE surface tension pens.

Application Conditions

The lacquers were applied by a 24 μm wire rod and cured by means of UV dryer, medium pressure Hg lamp, in 3 passes. The total UV curing energy, dose & intensity, were measured with an EIT UV Power Puck II having four UV light sensitive cells and are listed in Table 7.

TABLE 7

Intensity UV lamps used.

| UV detection cell | UV dose [mJ/cm2] | UV intensity [mW/cm2] |
|---|---|---|
| UVA | 510 | 184 |
| UVB | 400 | 148 |
| UVC | 160 | 59 |
| UVV | 610 | 208 |

Ink Adhesion

Adhesion testing method was derived from ISO 2409: 2007. Deviations from the norm were as following: A cross-cut was made on the cured film with a BYK 5126 cross-cut tester. A strip of 20 mm wide and 40 mm long tape was applied on the test surface whilst being pressed thoroughly in place by hand to avoid air bubbles. The tape used was TESA 4104 (2.3 N/cm adhesion to steel). The adhesive tape was then removed in a single backwards motion at an angle of approximately 60°. The adhesion data are reported according to the ISO 2409 norm (5=poor adhesion, 0=good adhesion).

Ink Formulation

The formulations are shown in Table 8.

TABLE 8

Ink formulations.

| Example | C2(comp) | Ex 7 | Ex 8 |
|---|---|---|---|
| AgiSyn 230A2 | 8.7 | 8.7 | 8.7 |
| Tri-Ac (III) | 25 | 0 | 0 |
| Mono-Az-di-Ac (I) | 0 | 46.3 | 0 |
| Di-Az-mono-Ac (II) | 0 | 0 | 25 |
| AgiSyn 2837 | 21.3 | 0 | 21.3 |
| AgiSyn 2816 | 45 | 45 | 45 |
| TOTAL parts by weight | 100.0 | 100.0 | 100.0 |
| TOTAL AZIRIDINE CONTENT (mol/kg) | 0.000 | 0.265 | 0.525 |

The adhesion results are shown in Table 9.

TABLE 9

The adhesion of examples Comp Ex 2 and Examples 7-8 to corona treated rigid PP.

| | C2(comp) | 7 | 8 |
|---|---|---|---|
| TOTAL AZIRIDINE CONTENT (mol/kg) | 0.000 | 0.265 | 0.525 |
| TESA 4104 | 5 | 2 | 2 |

The adhesion of the ink compositions that contain aziridine groups is remarkably improved compared to ink composition that contains no aziridine groups.

Comparative Experiment of Aziridine Functional UV Curable Compounds that Show a Genotoxic Response.

Comp Ex 3: TMP(9EO)TA (AgiSyn 2858) functionalised with 0.5 eq. PI via Michael addition resulting in a compound not containing a functional group with structural unit A A stainless steel reactor was charged with 710.7 g of TMP (9EO)TA AgiSyn 2858 and 0.38 g of phenothiazine. The reactor contents were heated to 35° C. When the reactor contents had reached a temperature of 35° C. a mixture of 87.8 g propyleneimine and 87.8 g of water were added to the reactor. The duration of this addition was 1 hour. After addition of the propyleneimine/water mixture was completed the reactor contents were heated to 45° C. for 20 hours. A sample of the reaction mixture was analysed to determine the free PI content. This was found to be less than 1 ppm of free PI. The contents of the reactor were then discharged. The reaction mixture was transferred to a separate glass reactor and the water in the reaction mixture was removed by heating the mixture to 50° C. and by reducing the pressure to 50 mbar. The water distilled off during 2 hours under these conditions to yield the final product. C4 and C5 have been synthesized according a similar procedure adjusting the amount of propyleneimine reflecting the stoichiometry.

The following aziridine functionalised multifunctional acrylate compounds were tested to compare their adhesion properties:

Comparative Experiment 3: TMP9EOTA (trimethylolpropane triacrylate with 9 ethoxylate groups) functionalised with 0.5 eq. PI via Michael addition resulting in a compound not containing a functional group with structural unit A Genotoxicity Test Results:

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration→ | 10 | 25 | 50 | 10 | 25 | 50 | 10 | 25 | 50 | 10 | 25 | 50 |
| Comp Ex 3. | 1.1 | 1.3 | 1.3 | 1.3 | 1.6 | 1.8 | 1.1 | 1.4 | 1.4 | 1.1 | 1.7 | 2.4 |

Formulation

The Comp Ex 3 has been formulated with the ingredients listed in Table 10. The adhesion data are listed in Table 11. Resin refers to the amount of comparative example 3.

TABLE 10

| Formulation C3 | | |
|---|---|---|
| Ingredients | Parts by weight | |
| Resin | 15.5 | Replaced per ink |
| Irgalite Rubine D4240 | 16.7 | Pre-mixed pigment paste |
| TMPTA 3EO | 25.2 | |
| Solsperse 39000 | 3.1 | |
| TMPTA 3EO P | 13.2 | Pre-mixed initiator paste |
| DPHA | 13.3 | |
| AS 703 P | 8.7 | |
| TegoAirex 920 | 0.3 | |
| Irgacure 127 | 2.0 | |
| Irgacure 819 | 2.0 | |

The adhesion was tested according to the adhesion test used for flexible plastic substrates described earlier. The results are listed in Table 11.

TABLE 11

| Adhesion test data C3 | |
|---|---|
| Example | C3 |
| Mw (theoretical) | 748 |
| Aziridine content in ink | 0.107 mol/kg |
| Scapa 1112 | 80 |
| 3M Scotch 610 | 100 |
| Scapa 1112 | 5 |
| 3M Scotch 610 | 100 |

The results in the table indicate that the adhesion of the inks containing aziridine functionalized polyacrylates is good (almost no lift-off). However, this Comparative Experiment expresses genotoxic activity as determined by the Toxys test as described above.

Migration

Test Method

The analysis of the extractables was using gradient elution and PDA/CAD/ESI-TOF-MS detection LC System: Agilent 1290 Infinity II Detector #1: Agilent 1290 Infinity II PDA Detector #2: Agilent 1260 ELSD Detector #3: Agilent Funnel 6550 Q-TOF-MS Column: Waters C18 T3, 100*2.1, 1.8 um Injection 1 μl volume:

Gradient:

| Time (min) | Flowrate (ul/min) | % A | % B | % C |
|---|---|---|---|---|
| 0 | 500 | 75 | 25 | 0 |
| 10 | 500 | 10 | 90 | 0 |
| 11 | 500 | 10 | 50 | 40 |
| 12 | 500 | 10 | 90 | 0 |
| 13 | 500 | 75 | 25 | 0 |
| 16 | 500 | 75 | 25 | 0 |

A = $H_2O$ (10 mM NH4CH3COO, pH 9.0), B = Acetonitrile, C = THF

A=$H_2O$ (10 mM NH4CH3COO, pH 9.0), B=Acetonitrile, C=THF

Samples were extracted with acetonitrile for 1 week. Standards were prepared in acetonitrile (4-point calibration curve). Only the amount of aziridine-functional multifunctional acrylics were measured. Other migratables were not analysed.

Ink Formulations

The formulations used are listed in Table 12 below. C4 is a Comparative Experiment containing no aziridine functionality while ink 9 and 10 are Examples according to the invention.

TABLE 12

| Formulations used for the migration tests. | | | | |
|---|---|---|---|---|
| Formulations | Aziridine (mol/kg) | C4 | 9 | 10 |
| Tri-Ac (III) (3:0 acrylate:aziridine) | 0 | 25.0 | | |
| Mono-Az-Di-Ac (I) (2:1 acrylate:aziridine) | 1.04 | | 25.0 | |
| Di-Az-Mono-Ac (II) (1:2 acrylate:aziridine) | 2.08 | | | 25.0 |
| AgiSyn 2836 | | 2.5 | 2.5 | 2.5 |
| AgiSyn 2837 | | 29.5 | 29.5 | 29.5 |
| Pigment concentrate | % | 33.0 | 33.0 | 33.0 |
| Irgalite Rubine D 4240 | 15.0 | | | |
| AgiSyn 2836 | 16.3 | | | |
| TegoAirex 920 | 0.1 | | | |
| Genorad 16 | 0.1 | | | |
| Solsperse 39000 | 1.5 | | | |
| Initiator mix | % | 10.0 | 10.0 | 10.0 |
| Omnirad EHA | 4.0 | | | |
| Omnirad TPO-L | 2.0 | | | |
| Omnirad 819 | 2.0 | | | |
| Omnirad 754 | 2.0 | | | |
| TOTAL | | 100.0 | 100.0 | 100.0 |
| TOTAL AZIRIDINE CONTENT (mol/kg) | | 0.00 | 0.26 | 0.52 |

Results

Table 13 lists the amount of extractables.

TABLE 13

| Amount of extractables (mg/kg) as measured by HPLC. | | | | |
|---|---|---|---|---|
| Example | Plain 50LL210 BOPP | C4 | 9 | 10 |
| Tri-Ac (III) | 5* | 70 | | |
| Mono-Az-di-Ac (I) | 5* | | 4.6 | |
| Di-Az-Mono-Ac (II) | 5* | | | 11 |

*Blanc samples contained a small amount of the tri-Acrylic most probably due to contamination between the sample made with tri-Ac and the blanc BOPP sheet.

The results show that the aziridine functionalised multifunctional acrylates show substantially less migration than the non-aziridine functionalised multifunctional acrylate.

Synthesis of BGE-PI Adduct:

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

Synthesis of an Aziridine-Functional UV Curable Compound (IV)

A reaction product with as main components di-Az-tri-Ac and mono-Az-hexa-Ac (this reaction product is further referred to as compound (IV)) was prepared by placing BGE-PI adduct (12.0 gram), Agisyn 2824 (42.4 gram), butylated hydroxytoluene (0.06 gram), phenothiazine (0.01 gram), and a reactive diluent (Agisyn 2837, 15 gram) in a flask and heating this mixture to 50° C. under mild stirring. In a dropping funnel a mixture of Agisyn 2837 (5 gram) and Desmodur® N3600 (25.6 gram) was placed. Next, bismuth neodecanoate (0.02 gram) was added to the reaction mixture and the mixture in the dropping funnel was added in 30 minutes. After this, the mixture was stirred at 50° C. and the progress of the reaction was monitored by disappearance of the NCO groups by IR. The calculated molecular weight of the theoretical main components was confirmed with MALDI-TOF-MS and is shown below:

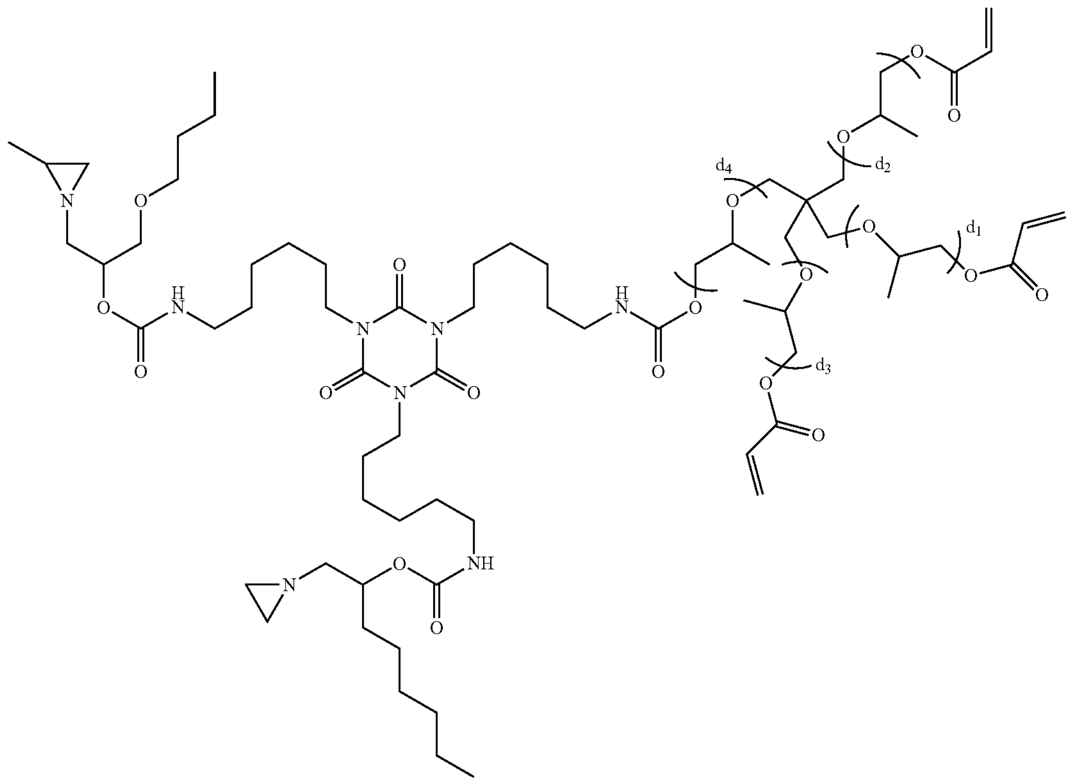

In this structure $d_1+d_2+d_3+d_4=5$

Calcd. [M+Na+]=1489.89 Da; Obs. [M+Na+]=1489.83 Da.

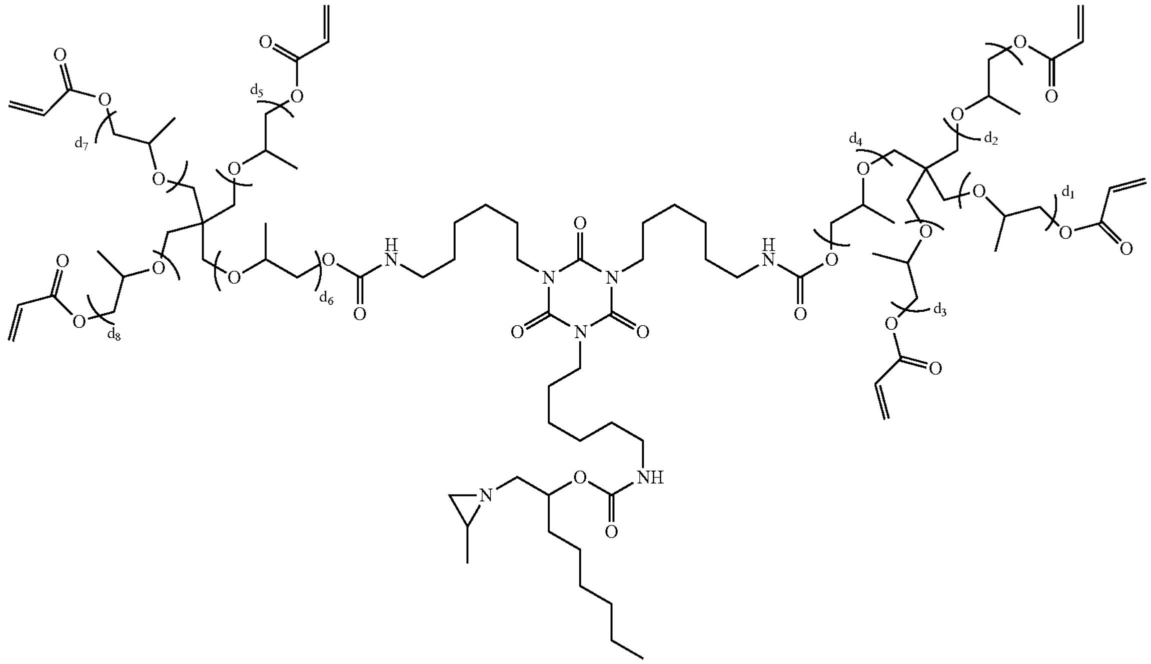

In this structure $d_1+d_2+ds+d_4+d_5+d_6+d_7+d_e=10$

Calcd. [M+Na+]=1891.05 Da; Obs. [M+Na+]=1890.90 Da.

The following component with a mass below 580 Da was determined by LC-MS and quantified:

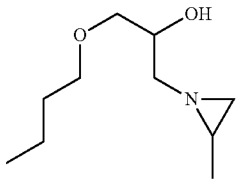

was present in the composition at less than 0.01 wt %.

Genotoxicity Test Results:

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration→ | 10 | 25 | 50 | 10 | 25 | 50 | 10 | 25 | 50 | 10 | 25 | 50 |
| Compound IV | 1.1 | 1.3 | 1.4 | 1.0 | 1.0 | 1.5 | 1.3 | 1.5 | 1.9 | 1.0 | 1.3 | 1.8 |

All values in this table show a negative induction level of the biomarkers of lower than a 2.0-fold induction at 10, 25 and 50% cytotoxicity in the absence and presence of rat S9 liver extract-based metabolizing systems and demonstrate that compound IV shows weakly positive induction of genotoxicity.

Ink-Performance of Aziridine-Functional UV Curable Compound (IV)

Preparation of Formulations

Pigment Paste:

The ingredients listed in Table 14 were added into a HDPP jar and mixed thoroughly using a speedmixer (DAC 150.1 FV, Hauschield GmbH) for 2 min @3500 rpm. Next, a grinding step by triple roll mill (Exact 80, Exact GmbH) until the fineness was <1 μm, as determined by Hegman Gage according to ASTM D1210, was employed.

TABLE 14

| Formulation: | % w/w | Producer |
|---|---|---|
| NeoRad P-50 | 10.4 | DSM NV |
| AgiSyn 2836P | 10.1 | DSM NV |
| 3 Solsperse S 39000 | 2.2 | Lubrizol Corp |
| Genorad 16 | 0.1 | Rahn AG |
| Irgalith Rubine D4240 | 17.2 | BASF SE |
| | 100.0 | |

Initiator Mixture:

The ingredients listed in Table 15 were added into a HDPP jar and heated to approximately 60° C. for an hour, or longer if needed to dissolve all solid particles. Once all ingredients were dissolved, the mixture was mixed thoroughly using a speedmixer (DAC 150.1 FV, Hauschield GmbH) for 2 min @3500 rpm.

TABLE 15

| Formulation: | % w/w | Producer |
|---|---|---|
| Omnipol ASA | 46.0 | IGM Resins BV |
| Omnipol TX | 33.0 | IGM Resins BV |
| Omnipol TPO-L | 20.0 | IGM Resins BV |
| Genorad 16 | 1.0 | Rahn AG |
| | 100.0 | |

Let Down:

The ingredients listed in Table 16 were added into a HDPP jar and mixed thoroughly using a speedmixer (DAC 150.1 FV, Hauschield GmbH) for 2 min @3500 rpm.

TABLE 16

| Formulation: | A Reference % w/w | B Model resin % w/w | Producer |
|---|---|---|---|
| Pigment paste | 40.0 | 40.0 | |
| AgiSyn 701P | 13.0 | 13.0 | DSM NV |
| AgiSyn 708 | 10.0 | — | DSM NV |
| Compound IV | — | 10.0 | — |
| AgiSyn 2836P | 17.0 | 17.0 | DSM NV |
| Initiator Mix | 20.0 | 20.0 | |
| | 100.0 | 100.0 | |

Application of Formulations:

The formulations obtained were applied on commercially available foils; CDC 28 (BOPP ex Treofan GmbH) and Mylar 813 (PET ex DuPont Teijin Films Ltd) by a C1-5 printer (IGT Testing Systems Inc) with a color density ranging between 1.3 to 1.5 according ATSM D7305 measured by DensiEye 700 (ex X-Rite Inc).

Curing of the Formulations:

Within 1 minute after application the formulations were cured on a UVio curing rig with a conveyor belt speed of 30 m/min equipped with a Light Hamer 10Mark II equipped with a H-bulb operating @50% power (Heraeus Inc, Hg doped UV lamp generating 394 $mJ/cm^2$ and 4276 $mW/cm^2$ total dose combined UVA, UVB, UVC and UVV as determined with am Power Puck II (EIT Inc)).

Testing of the Cured Formulations:

The adhesion was determined 24 hours after printing, similar to ASTM D3359 but without the scratch or cross hatch marks. The tape used was TESA 57341 and testing occurred in duplo. The rating given was obtained by visual determination as % adhesion, rounded to 5% level, the average of the duplo measurement was reported in table 17.

TABLE 17

| | Formulation: | |
|---|---|---|
| | A Reference (Comp 5) % adhesion | B Compound IV Resin (Ex 11) % adhesion |
| CDC 28 | 5 | 95 |
| Mylar 813 | 70 | 100 |

The invention claimed is:

1. A compound (I) having a molecular weight, determined using MALDI-TOF mass spectrometry, in a range from 600 to 5000 Dalton, consisting of a), b) and c), wherein a) a group W, b) at least one functional group A, and c) at least one functional group B, and wherein each one of the functional groups A and B is connected to the group W, and wherein a summed amount of the number of functional groups A and the number of functional groups B in compound (I) is from 2 to 13, and wherein the group W consists of at least one functionality selected from the group consisting of aliphatic hydrocarbon functionality, cycloaliphatic hydrocarbon functionality, aromatic hydrocarbon functionality, isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof, and wherein the functional groups A has structural formula A:

(A)

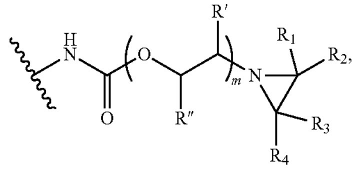

wherein $R_1$ is H, $R_2$, $R_3$ and $R_4$ are independently chosen from H, methyl or ethyl, m is 1 to 6, R' and R" are according to (1) or (2):

(1) R'=H or an aliphatic hydrocarbon group containing from 1 to 14 carbon atoms, and R"=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$ 0 (C═O) R''', $CH_2$—O R'''', or $CH_2$ (OCR''''HCR'''''H)~OR'''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R''''' independently being H or an aliphatic hydrocarbon group containing from 1 to 14 carbon atoms and R'''''' being an aliphatic hydrocarbon group containing from 1 to 4 carbon atoms, (2) R' and R" form together a saturated cycloaliphatic hydrocarbon group containing from 5 to 8 carbon atoms; and the functional groups B has structural formula B:

(B)

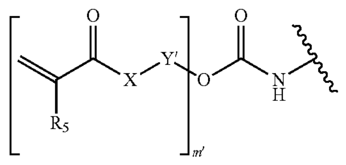

m' is an integer from 1 to 6, $R_5$ is H or methyl, X is O or NH, and

Y' is a collection of at most 100 atoms covalently connected in linear or branched configuration which collection of atoms consists of i) carbon and hydrogen atoms, or ii) carbon, hydrogen and oxygen atoms.

2. The compound (I) of claim 1, wherein $R_2$ is H, $R_3$ is $CH_3$ and $R_4$ is H.

3. The compound according to claim 1, wherein m is 1, R' is H and R"=an alkyl group containing from 1 to 4 carbon atoms.

4. The compound (I) of claim 1, wherein $R_5$ is H.

5. The compound (I) of claim 1, wherein X is O.

6. The compound (I) of claim 1, wherein the summed amount of the number of functional groups A and the number of functional groups B in compound (I) is from 3 to 10.

7. The compound (I) of claim 1, wherein the molecular weight is in a range of from 600 Daltons to 3800 Daltons.

8. A 100% radiation curable composition containing less than 5 wt. % of water and volatile organic solvent by weight of a solids content of the composition and comprises i) at least one compound (I) of claim 1, and ii) at least one compound (II) selected from the group consisting of polyester (meth)acrylates, polyether (meth)acrylates, epoxy (meth)acrylates, amino (meth)acrylates, polycarbonate (meth)acrylates, (poly)urethane (meth)acrylates, and (meth) acrylated (meth)acrylics.

9. The composition of claim 8, wherein the compound (II) has (meth)acryloyl ester groups.

10. The composition of claim 8, wherein the compound (II) has acryloyl ester groups.

11. The composition of claim 8, wherein the amount of the compound (I) is least 2 wt. % and at most 40 wt. % relative to a total amount of the composition, and an amount of compound (II) is at least 60 wt. % and at most 90 wt. %, relative to the total amount of the composition.

12. The composition of claim 8, wherein a molar ratio of aziridinyl groups of the following structural formula

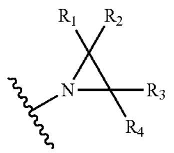

to ethylenically unsaturated bonds in the compound (I) is in a range of from 1:5 to 1:1.

13. The composition of claim 8, wherein the composition is UV-curable.

14. An ink composition comprising the composition of claim 8.

* * * * *